(12) United States Patent
Ilekti et al.

(10) Patent No.: US 8,911,714 B2
(45) Date of Patent: *Dec. 16, 2014

(54) COSMETIC HEAT TREATMENT METHOD USING A STRUCTURING AGENT

(75) Inventors: Philippe Ilekti, Maison-Alfort (FR); Xavier Blin, Paris (FR)

(73) Assignee: L'Oreal, Paris (FR)

( * ) Notice: Subject to any disclaimer, the term of this patent is extended or adjusted under 35 U.S.C. 154(b) by 616 days.

This patent is subject to a terminal disclaimer.

(21) Appl. No.: 13/003,065

(22) PCT Filed: Jul. 22, 2009

(86) PCT No.: PCT/FR2009/051478
§ 371 (c)(1),
(2), (4) Date: Apr. 8, 2011

(87) PCT Pub. No.: WO2010/010305
PCT Pub. Date: Jan. 28, 2010

(65) Prior Publication Data
US 2011/0176852 A1     Jul. 21, 2011

Related U.S. Application Data

(60) Provisional application No. 61/096,393, filed on Sep. 12, 2008.

(30) Foreign Application Priority Data

Jul. 24, 2008 (FR) .................................. 08 55085

(51) Int. Cl.
| | | |
|---|---|---|
| A61Q 1/06 | (2006.01) | |
| A61Q 1/04 | (2006.01) | |
| A45D 40/08 | (2006.01) | |
| A61K 8/81 | (2006.01) | |
| A45D 40/18 | (2006.01) | |
| A45D 40/20 | (2006.01) | |

(52) U.S. Cl.
CPC *A61Q 1/06* (2013.01); *A45D 40/08* (2013.01); *A61K 8/8105* (2013.01); *A61K 8/8152* (2013.01); *A45D 40/18* (2013.01); *A45D 40/20* (2013.01); *A45D 2200/155* (2013.01); *A61K 2800/884* (2013.01)
USPC ............................................. 424/64; 424/401

(58) Field of Classification Search
None
See application file for complete search history.

(56) References Cited

U.S. PATENT DOCUMENTS

| | | | |
|---|---|---|---|
| 2,676,182 A | 4/1954 | Daudt et al. | |
| 3,148,125 A | 9/1964 | Strianse et al. | |
| 3,627,851 A | 12/1971 | Brady | |
| 3,645,705 A | 2/1972 | Miller et al. | |
| 3,772,247 A | 11/1973 | Flannigan | |
| 4,935,484 A | 6/1990 | Wolfgruber et al. | |
| 5,082,706 A | 1/1992 | Tangney | |
| 5,110,890 A | 5/1992 | Butler | |
| 5,156,911 A | 10/1992 | Stewart | |
| 5,221,534 A | 6/1993 | DesLauriers et al. | |
| 5,248,739 A | 9/1993 | Schmidt et al. | |
| 5,302,685 A | 4/1994 | Tsumura et al. | |
| 5,319,040 A | 6/1994 | Wengrovius et al. | |
| 5,500,209 A | 3/1996 | Mendolia et al. | |
| 5,519,063 A | 5/1996 | Mondet et al. | |
| 5,736,125 A | 4/1998 | Morawsky et al. | |
| 5,783,657 A | 7/1998 | Pavlin et al. | |
| 5,874,069 A | 2/1999 | Mendolia et al. | |
| 5,919,441 A | 7/1999 | Mendolia et al. | |
| 5,981,680 A | 11/1999 | Petroff et al. | |
| 5,998,570 A | 12/1999 | Pavlin et al. | |
| 6,051,216 A | 4/2000 | Barr et al. | |
| 6,478,493 B1 | 11/2002 | Cepeda et al. | |
| 6,949,504 B2 * | 9/2005 | Mondet et al. ..................... 514/1 |
| 2002/0004036 A1 * | 1/2002 | Piot et al. ..................... 424/70.7 |
| 2002/0005562 A1 | 1/2002 | Kim et al. | |
| 2004/0175338 A1 * | 9/2004 | Filippi et al. ..................... 424/64 |
| 2005/0031400 A1 * | 2/2005 | Marcotte et al. ............. 401/129 |
| 2005/0050328 A1 | 3/2005 | Mizrah | |
| 2005/0287105 A1 | 12/2005 | Blin et al. | |
| 2006/0008441 A1 | 1/2006 | Kanji et al. | |

(Continued)

FOREIGN PATENT DOCUMENTS

| | | |
|---|---|---|
| DE | 101 50 619 | 4/2003 |
| EP | 0 550 745 | 7/1993 |

(Continued)

OTHER PUBLICATIONS

U.S. Appl. No. 13/009,975, filed Jan. 20, 2011, Ilekti, et al.

(Continued)

*Primary Examiner* — Jyothsna Venkat

(74) *Attorney, Agent, or Firm* — Oblon, Spivak, McClelland, Maier & Neustadt, L.L.P.

(57) ABSTRACT

A method of makeup and/or non-therapeutic care for non-fibrous human keratin material, particularly the skin, the lips, or the nails, having the steps of: bringing an outer surface of a piece of solid cosmetic composition into contact with, or near, a heating device so as to heat said piece in a localized manner with a view to essentially softening only said outer surface and lowering the dynamic rub coefficient thereof; and then applying the outer surface of the thus-heated composition onto the area to be treated, the solid cosmetic composition including, in a physiologically acceptable medium, at least 4 wt % of at least one structuring agent selected from among waxes, organophilic clays, hydrophobic pyrogenic silicas, alkylated guar gums, hydrophobic celluloses, block copolymers, and the mixtures thereof.

13 Claims, 3 Drawing Sheets

(56) References Cited

U.S. PATENT DOCUMENTS

| | | |
|---|---|---|
| 2007/0031361 A1 | 2/2007 | Herrmann et al. |
| 2007/0053859 A1 | 3/2007 | Bui et al. |
| 2007/0286665 A1 | 12/2007 | Bouix et al. |
| 2008/0143214 A1 | 6/2008 | McNamara et al. |
| 2008/0152678 A1 | 6/2008 | Shah et al. |
| 2010/0316587 A1 | 12/2010 | Barba et al. |

FOREIGN PATENT DOCUMENTS

| | | |
|---|---|---|
| EP | 0 708 114 | 4/1996 |
| EP | 1 266 647 | 12/2002 |
| EP | 1 454 612 | 9/2004 |
| FR | 2 888 498 | 1/2007 |
| FR | 2 894 472 | 6/2007 |
| FR | 2 918 272 | 1/2009 |
| FR | 2 926 022 | 7/2009 |
| JP | 2007 269763 | 10/2007 |
| WO | 01 19333 | 3/2001 |
| WO | 02 47619 | 6/2002 |
| WO | 02 056847 | 7/2002 |
| WO | 2003 106614 | 12/2003 |
| WO | 2005 075542 | 8/2005 |
| WO | 2009 080955 | 7/2009 |
| WO | 2009 104133 | 8/2009 |

OTHER PUBLICATIONS

Anonymous: "Brillants a levres," Research Disclosure Journal, ISSN 0374-4353, vol. 526, No. 20, total 8 pages, (Jan. 25, 2008) XP 007137951 (with partial English translation).

International Search Report issued Apr. 8, 2010 in PCT/FR09/051478 filed Jul. 22, 2009.

International Search Report issued Mar. 9, 2010 in PCT/FR09/051474 filed Jul. 22, 2009.

U.S. Appl. No. 13/054,681, filed Jan. 18, 2011, Ilekti, et al.

U.S. Appl. No. 12/988,465, filed Oct. 18, 2010, Ilekti, et al.

\* cited by examiner

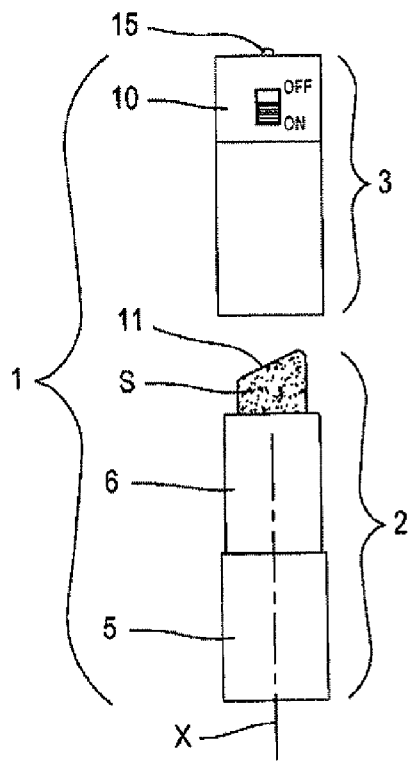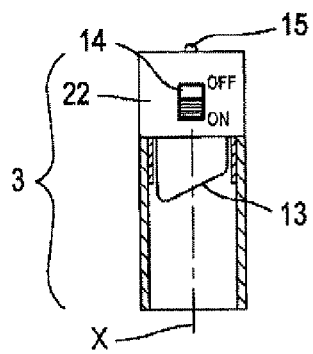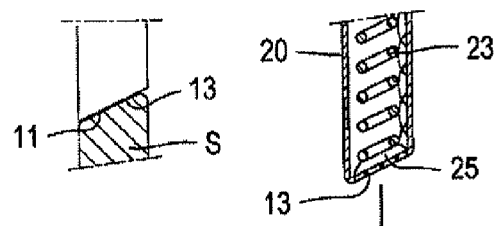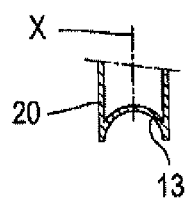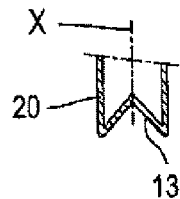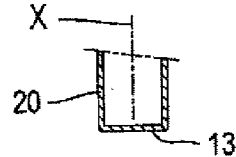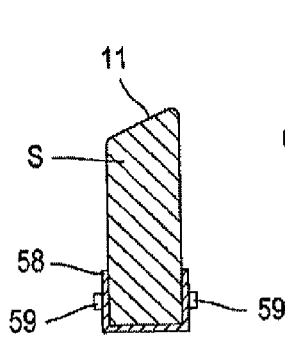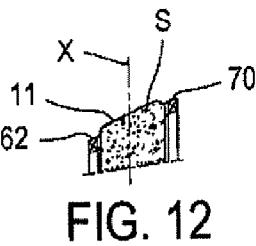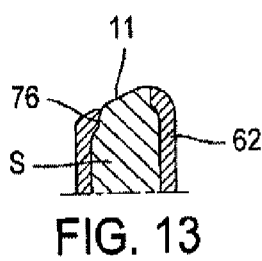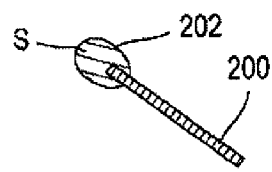

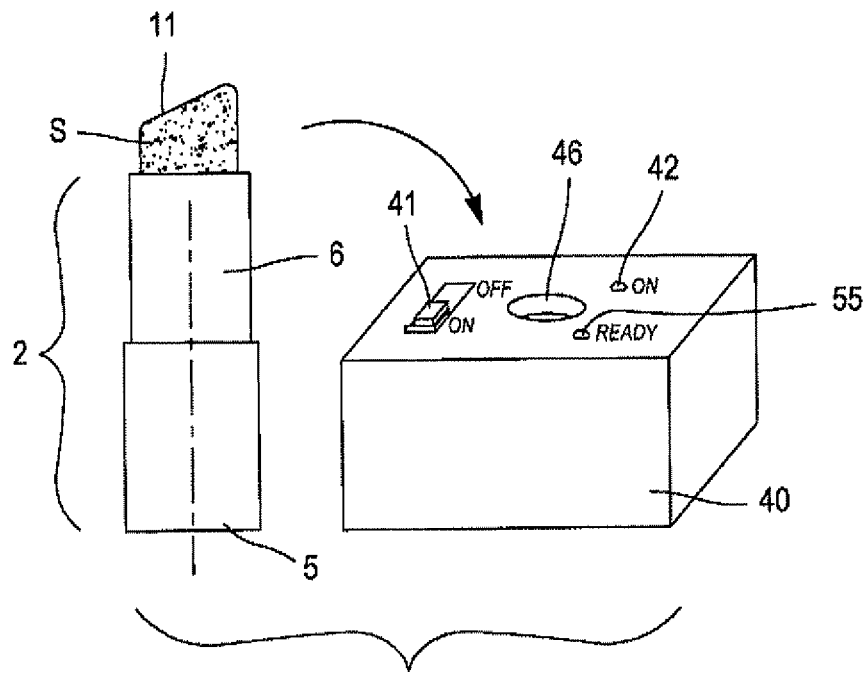
FIG. 8
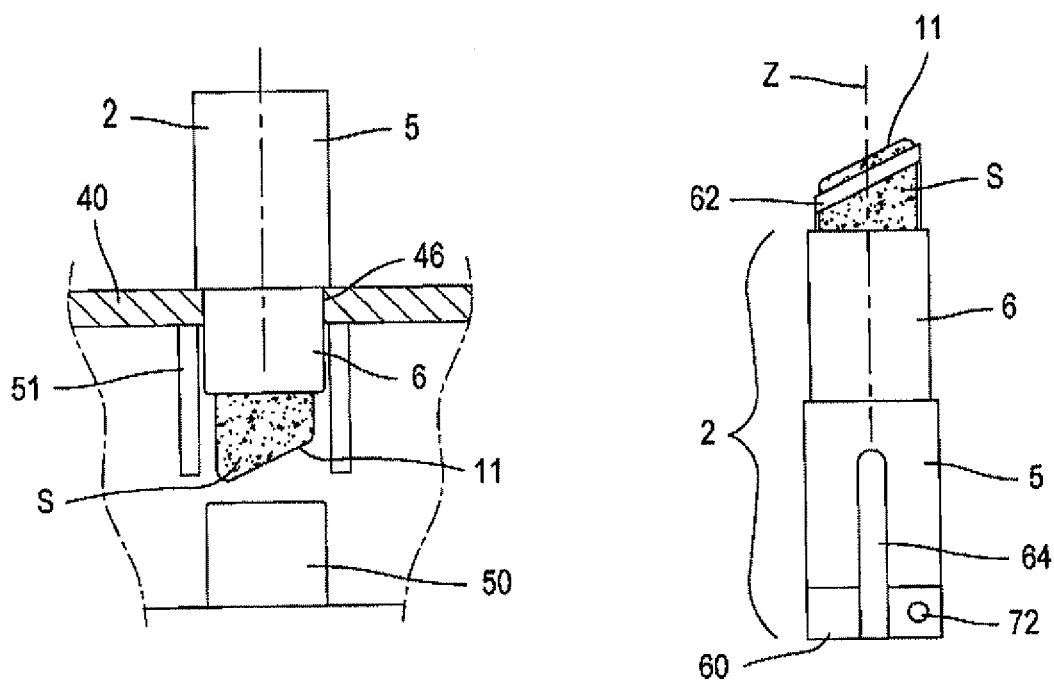
FIG. 9
FIG. 11

COSMETIC HEAT TREATMENT METHOD USING A STRUCTURING AGENT

The present invention relates to the field of caring for and/or making up human keratin materials and more particularly the skin and/or the lips.

The development of formulations intended for making up and/or caring for the skin and/or the lips, which have satisfactory properties in terms of application, comfort, staying power and coverage, but also in terms of the makeup effect, for instance the gloss, is a permanent objective.

As regards the lips, lipsticks, which appeared at the start of the last century, are now firmly established and are acknowledged by users as the favored mode for making up their lips. This application mode offers users a means of choice, in terms of coverage of the lips and diversity of the colors.

Needless to say, this galenical form must moreover satisfy mechanical requirements, on the one hand, so as to ensure the glidance and strength of the wand during application and to avoid it breaking, and transfer qualities, on the other hand, so as to ensure a comfortable application and also a sufficient and good-quality deposit on the lips.

Now, it is known that a certain number of ingredients capable of affording the product advantageous characteristics, for example in terms of the makeup effect, may on the other hand harm the application qualities, or may even make this application impossible.

Thus, it is known that it is possible to give a glossy nature and to improve the comfort of the makeup film via the presence of oils in this type of composition. However, these starting materials moreover have the drawback of migrating. Consequently, it is important to prevent the manifestation of this migration phenomenon in the makeup deposit into which they are incorporated in order to ensure visual rendering of its contours. This requirement is conventionally satisfied by combining these oils with one or more structuring agents that may be inorganic, for instance bentone, or organic, such as waxes. Unfortunately, the use of these structuring agents is liable to affect the comfort qualities on application, especially in terms of the glidance. Conventional makeup and/or care compositions are thus formulated so as to achieve a compromise with regard to these two requirements.

For obvious reasons, it would be advantageous to have available a makeup mode that can overcome this type of constraint.

In particular, there is a need to be able to fully exploit the cosmetic properties of certain ingredients without being elsewhere affected by their impact on the application qualities, especially in terms of the glidance of the composition into which they are incorporated.

There is also a need to improve the performance of a cosmetic product in the form of a solid mass, whether in sensory terms and/or in terms of the makeup result, while at the same time conserving for the product mechanical properties that are compatible with conditioning as a wand or in another solid form and with application by friction on the surface to be treated.

In particular, there is a need for a makeup mode which, on the one hand, is capable of affording a glossy effect and/or comfort via the use of oils and which is moreover free of the migrating effect specific to these oils, and which, on the other hand, also proves to have advantageous qualities in terms of glidance on a keratin material.

The object of the invention is precisely to propose a novel makeup and/or care mode that can satisfy all of the above-mentioned requirements.

Thus, according to a first of its aspects, a nontherapeutic process for making up and/or caring for human keratin materials, especially the skin, the lips or the nails, in which:
an outer surface of a piece of solid cosmetic composition is brought into contact with or in the vicinity of a heating device so as to heat said piece locally in order to soften essentially only said outer surface and to lower its coefficient of dynamic friction, and
the outer surface of the composition thus heated is then applied to the area to be treated,
said solid cosmetic composition comprising, in a physiologically acceptable medium, at least 4% by weight of at least one structuring agent chosen from waxes, organophilic clays, hydrophobic fumed silicas, alkyl guar gums, hydrophobic celluloses, block copolymers and mixtures thereof, said composition being different than a composition defined as follows, the amounts being expressed as weight percentages:

| | |
|---|---|
| BHT | 0.06 |
| PEG-45/DODECYL GLYCOL COPOLYMER | 6 |
| OCTYLDODECYL NEOPENTANOATE | 18 |
| POLYBUTENE | 15 |
| TRIISOSTEARIN | 7 |
| OCTYLDODECYL/PPG-3 MYRISTYL ETHER DIMER DILINOLEATE | 1 |
| BIS-DIGLYCERYL POLYACYLADIPATE-2 | 15 |
| ISOSTEARYL ISOSTERATE | 10 |
| DISTEARDIMONIUM HECTORITE | 1 |
| YELLOW 6 LAKE | 7 |
| RED 7 | 4 |
| TITANIUM DIOXIDE | 1 |
| POLYETHYLENE | 5 |
| MICROCRYSTALLINE WAX | 7 |
| MICA | 2.94 |

According to another of its aspects, a subject of the present invention is a nontherapeutic process for making up and/or caring for non-fibrous human keratin materials, especially the skin, its mucous membranes or the nails, comprising the steps consisting in:
bringing an outer surface of a piece of solid cosmetic composition into contact with or in the vicinity of a heating device so as to heat said piece locally in order to soften essentially only said outer surface and to lower its coefficient of dynamic friction, and
then applying the outer surface of the composition thus heated onto the area to be treated, said solid cosmetic composition comprising, in a physiologically acceptable medium:
at least 4% by weight, relative to the total weight of the composition, of at least one structuring agent chosen from waxes, organophilic clays, hydrophobic fumed silicas, alkyl guar gums, hydrophobic celluloses and block copolymers, and mixtures thereof, and
at least 10% by weight of glossy oil(s), relative to the total weight of the composition, said oil being a hydrocarbon-based or silicone oil with a molecular mass of greater than 400 g/mol.

According to one particular embodiment of the invention, the process is a makeup process.

According to one particular embodiment, the softened outer surface is brought directly into contact with the area to be treated, and in particular with keratin materials.

In other words, no applicator is used to apply the softened composition.

For the purposes of the present invention, the term "solid", especially at room temperature (for example 20° C.), refers to a composition of high consistency, which keeps its shape during storage, and which especially does not flow under its own weight.

When the composition is in the form of a stick, the outer surface may be defined as the extremity thereof.

According to one particular embodiment, the process according to the present invention is such that the composition is in the form of a wand, especially with a diameter of greater than or equal to 8 mm.

According to yet another embodiment, the process according to the present invention is such that the composition is a lipstick.

It is advantageously characterized by a hardness as defined below.

According to yet another aspect, the invention relates to a kit comprising:
 a composition as defined previously, and
 a heating device for locally heating a surface of a piece of said composition.

The piece of composition may be permanently in contact with or close to the heating device, and this heating device may be activated before applying the composition, to raise the temperature of the outer surface of the piece of composition. As a variant, the piece of composition is brought into contact with or close to the heating device only for the use, for the purpose of applying the composition.

Thus, the invention may make it possible to heat at the surface, just before application, for example the top of the bevel of a lipstick wand made with a composition according to the invention, so as to allow deposition, even if the wand contains compounds that are sparingly suited to satisfactory cold application, these compounds affording increased performance in terms of staying power and/or gloss.

In examples of implementation of the invention, by heating the surface of the wand, its glidance and thus its application to the lips or the skin may be improved.

According to one particular embodiment, the composition used according to the invention has a temperature-sensitive coefficient of dynamic friction, of greater than or equal to 0.5 at 25° C. and better still greater than or equal to 0.6 at 25° C.

The solid composition advantageously has a hardness of greater than or equal to 80 Nm$^{-1}$ at 20° C., better still greater than or equal to 100 Nm$^{-1}$ or even 120 Nm$^{-1}$ at 20° C., which makes the wand mechanically strong and allows its conditioning, for example, in a conventional case comprising two parts that can rotate relative to each other to move the wand.

The coefficient of dynamic friction may be, at the temperature to which the composition is heated, less than or equal to 0.45 and better still 0.4.

The coefficient of dynamic friction, which is greater than or equal to 0.5 at 25° C. may thus become, for example, less than or equal to 0.45 at 45° C., i.e. it may reach a value comparable to certain known lipsticks intended for application at 25° C.

The invention may apply to a wand of product comprising an amount of texturing agent such that its application cold and/or without heating is difficult, virtually impossible or unpleasant. For such a wand of product, application after heating becomes possible, with particularly advantageous comfort or even gloss performance with regard to the presence of the oils it contains.

The product may be heated in various ways, for example by being exposed to infrared radiation or to wireless radiation.

The product may also be heated by blowing with hot air, by being exposed to ultrasonic vibrations or by heat transfer on contact with or close to a hot surface which, for example, bears radially against the outer surface, especially the end of the wand. The hot surface may also bear axially against the outer surface, especially the end of the wand. The hot surface may have a beveled, inverted cone or concave hollow shape, especially spherical.

The outer surface of the product may be heated to a temperature $T_f$ of greater than or equal to 40° C., or even greater than 45° C. or alternatively greater than 50° C. The outer surface may be heated to a temperature $T_f$ of between 40° C. and 95° C., better still 45° C. to 85° C. and better still 45° C. to 75° C.

The temperature of the application surface, especially of the end of the wand, should not lead to any risk of burning at the time of application. This is why a waiting time between the moment at which the end is heated and the application to the keratin materials may optionally be necessary.

The temperature difference between the heated outer surface and the portion of the product that remains solid may be greater than or equal to 5° C. and better still greater than or equal to 15° C. or 20° C., at least at the start of application, or even greater than 30° C.

Only the product may come into contact with the treated area during the application.

The heating device may be housed in a cap for closing the support, so as to allow the outer surface to be heated with the cap in place on the support. The heating device may also be housed elsewhere than in a cap for closing the support.

The heating device may be housed in a case on which the support may be engaged so that the heating may take place when the support is engaged in the case, especially a case comprising an aperture in which the piece of solid product may be engaged, preferably without the whole support being placed inside the case.

The heating device may be an integral part of the conditioning and application device.

The heating device may be arranged to come into contact with the outer surface.

The heating device may be arranged so that the piece of product passes through it, and may especially comprise a circular-shaped hot surface.

The heating device may comprise a control means allowing the user to control its functioning. This control means may comprise a switch present on the support or on a cap for closing the support.

The heating device may comprise an electrical resistance to heat a surface that may come into contact with or close to the application surface.

The heating device may comprise an infrared emitter arranged to subject the application surface to infrared light so as to heat it, and a wireless radiation emission means for raising the temperature of the outer surface, a fan for blowing hot air onto the outer surface or a source of ultrasound for heating the outer surface.

The heating device may also comprise at least two components that are capable, when mixed together, of producing an exothermic reaction.

The piece of product may be in the form of a wand and the outer surface may be defined by the end of the wand.

The heating device may comprise a source of electrical power comprising one or more batteries or accumulators.

The heating device may comprise an electric generator actuated by the user.

The heating device may comprise means for heating the piece of composition to a predefined temperature, despite the wear of said piece. This means may comprise an elastically deformable member, which ensures contact or a constant gap between the outer surface to be heated and the heating device, by compensating for the wear of the piece of composition.

These means may also comprise, where appropriate, a temperature sensor for adjusting the heating power, for example for increasing it if the outer surface is further away from the source of heat.

Coefficient of Dynamic Friction

To characterize the coefficient of dynamic friction of the product, a machine comprising a carriage that moves over a distance of 100 mm on ball bearings may be used.

Correct movement of the carriage is ensured by means of a rigid connection with moving crosshead of a traction-compression machine (TAXT2 from the company Rheo) placed horizontally, with a magnet attached to the back of the carriage.

The product S whose coefficient of dynamic friction it is sought to evaluate is cut at one end with a tungsten wire of diameter 250 μm by removing the wire relative to the stick at a speed of 100 mm/minute and perpendicular to its longitudinal axis so as to have a flat contact surface parallel to the sliding surface W.

A normal force Fn is applied thereto at the sliding surface W by means of a weight. This weight is such that the pressure exerted on the surface of the product S in contact with W is $7.9 \times 10^{-3}$ MPa.

The product may be in the form of a circular cylindrical wand.

In the case where the cross section of the wand is not circular, the stick is slid in the direction of the small axis of its cross section, by moving the large axis parallel to itself.

The coefficient of friction is defined as the ratio of the tangential force Ft applied to the body moving in the direction M to the normal force Fn experienced by this same body, as illustrated in FIG. 15.

In a friction test, a first transient phase of start of movement of the system and a second phase of continuous regime may be distinguished.

In the first phase, the tangential force increases to reach a maximum that corresponds to the start of movement of the system. This maximum corresponds to the static friction force, known as the static Ft, and makes it possible to define a coefficient of static friction ($\mu s$)

$$\mu s = \text{static } Ft/Fn$$

where Fn is the applied normal force.

The tangential force Ft then decreases to generally reach a more stable regime. The coefficient of dynamic friction is defined in this phase of the movement as the ratio of the dynamic friction force (tangential force) to the applied normal force (Fn):

$$\mu d = \text{dynamic } Ft/Fn$$

The coefficient of friction is a dimensionless magnitude, which depends on the two surfaces in contact and on the contact conditions.

The sliding surface is defined by artificial skin of reference Bio Skin Plate Black K275 from the company Maprecos, with a width greater than or equal to the cross section of the stick.

For a measurement at 25° C., the apparatus and the composition are both at 25° C.

The artificial skin is placed on the support that may be heated to the temperature at which it is desired to measure the coefficient of dynamic friction. The wand initially at a temperature of 25° C. is applied, for example to the artificial skin thus heated, for example to 45° C. if the measurement is to be taken at 45° C. The surface temperature of the artificial skin may be monitored with an optical thermometer.

In certain embodiments, the coefficient of dynamic friction of a composition according to the invention is greater than or equal to 0.6, or even 0.7 or even 0.8 at 25° C. The coefficient of dynamic friction at 25° C. of the compositions according to the invention may be less than or equal to 5.

The stick may have a diameter of 12.7 mm in the region of its area of contact with the sliding surface, but other values are possible, for example ranging from 7 mm to 50 mm.

Hardness Parameter

The compositions under consideration according to the invention are relatively hard at room temperature and, under the action of heat, become soft enough to be able to be applied.

The hardness may be measured at 20° C. via the cheese wire method, which consists in transversely cutting a wand of product, which is preferably a circular cylinder, by means of a rigid tungsten wire 250 μm in diameter, by moving the wire relative to the stick at a speed of 100 mm/minute. The hardness corresponds to the maximum shear force exerted by the wire on the stick at 20° C., this force being measured using a DFGHS 2 tensile testing machine from the company Indelco-Chatillon. The measurement is repeated three times and then averaged.

The average of the three values read using the tensile testing machine mentioned above, noted Y, is given in grams. This average is converted into newtons and then divided by L which represents the longest distance through which the wire passes. In the case of a cylindrical wand, L is equal to the diameter in meters.

The hardness is converted by the equation below:

$$(Y \times 10^{-3} \times 9.8)/L$$

For a measurement at a different temperature, the entire stick is heated to the temperature at which the hardness is to be measured.

According to this method, the hardness at 20° C. of examples of composition according to one aspect of the invention is greater than 80 $Nm^{-1}$, especially greater than 100 $Nm^{-1}$ and preferably greater than 120 $Nm^{-1}$.

A composition of the invention is cosmetically or dermatologically acceptable, i.e. it contains a nontoxic physiologically acceptable medium that can be applied to human lips. For the purposes of the invention, the term "cosmetically acceptable" refers to a composition of pleasant appearance, odor and feel that is suitable for use in cosmetics.

Structuring Agent

As stated previously, a composition according to the invention contains at least one structuring agent.

The term "structuring agent" means a compound that is capable of increasing the viscosity of the composition into which it is incorporated. The structuring agent especially makes it possible to obtain a composition that may have a texture ranging from fluid to solid textures.

A structuring agent or mixture of structuring agents may be present in the composition in a content ranging from 4% to 40% by weight and preferably ranging from 4% to 30% by weight relative to the total weight of the composition.

The process according to the invention is most particularly advantageous for the application of a composition comprising from 4% to 25% by weight of structuring agent(s).

The structuring agent according to the invention is chosen from:

waxes,
organophilic clays,
fumed silicas,
alkyl guar gums (with a C1-C6 alkyl group), such as those described in EP-A-708 114,
hydrophobic celluloses, block copolymers resulting especially from the polymerization or copolymerization of at least one monomer containing an ethylenic group, for instance the polymers sold under the name Kraton®, and mixtures thereof.

More preferentially, it is chosen from waxes, fumed silicas, organophilic clays and block copolymers such as Kraton®, and mixtures thereof.

According to one particular embodiment, the structuring agent is a mixture of waxes and of fumed silicas and/or organophilic clays.

a) Wax

The wax under consideration in the context of the present invention is generally a lipophilic compound that is solid at room temperature (25° C.), with a solid/liquid reversible change of state, having a melting point of greater than or equal to 30° C., which may be up to 200° C. and in particular up to 120° C.

In particular, the waxes that are suitable for the invention may have a melting point of greater than or equal to 45° C. and in particular greater than or equal to 55° C.

For the purposes of the invention, the melting point corresponds to the temperature of the most endothermic peak observed by thermal analysis (DSC) as described in ISO standard 11357-3; 1999. The melting point of the wax may be measured using a differential scanning calorimeter (DSC), for example the calorimeter sold under the name "MDSC 2920" by the company TA Instruments.

The measuring protocol is as follows:

A sample of 5 mg of wax placed in a crucible is subjected to a first temperature rise ranging from −20° C. to 100° C., at a heating rate of 10° C./minute, it is then cooled from 100° C. to −20° C. at a cooling rate of 10° C./minute and is finally subjected to a second temperature increase ranging from −20° C. to 100° C. at a heating rate of 5° C./minute. During the second temperature increase, the variation of the difference in power absorbed by the empty crucible and by the crucible containing the sample of wax is measured as a function of the temperature. The melting point of the compound is the temperature value corresponding to the top of the peak of the curve representing the variation in the difference in absorbed power as a function of the temperature.

The waxes that may be used in the compositions according to the invention are chosen from waxes that are solid at room temperature, of animal, plant, mineral or synthetic origin, and mixtures thereof.

As illustrations of waxes that are suitable for use in the invention, mention may be made especially of hydrocarbon-based waxes, for instance beeswax, lanolin wax and Chinese insect waxes, rice bran wax, carnauba wax, candelilla wax, ouricury wax, alfalfa wax, berry wax, shellac wax, Japan wax and sumach wax; montan wax, orange wax and lemon wax, microcrystalline waxes (such as the wax sold under the reference Microwax HW by the company Paramelt), paraffins and ozokerite; polyethylene waxes such as those sold under the name Performalene 500-L and Performalene 400 by the company New Phase Technologies, and the waxes obtained by Fisher-Tropsch synthesis.

Mention may also be made of the waxes obtained by catalytic hydrogenation of animal or plant oils with linear or branched $C_8$-$C_{32}$ fatty chains. Among these, mention may be made especially of isomerized jojoba oil such as the trans-isomerized partially hydrogenated jojoba oil manufactured or sold by the company Desert Whale under the trade reference Iso-Jojoba-50®, hydrogenated sunflower oil, hydrogenated castor oil, hydrogenated coconut oil, hydrogenated lanolin oil, and the bis(1,1,1-trimethylolpropane) tetrastearate sold under the name Hest 2T-4S® by the company Heterene. Mention may also be made of silicone waxes ($C_{30-45}$ Alkyl Dimethicone) and fluoro waxes.

It is also possible to use the waxes obtained by hydrogenation of castor oil esterified with cetyl alcohol, sold under the names Phytowax Ricin 16L64® and 22L73® by the company Sophim. Such waxes are described in patent application FR-A-2 792 190.

It is possible to use a $C_{20}$-$C_{40}$ alkyl (hydroxystearyloxy) stearate (the alkyl group comprising from 20 to 40 carbon atoms) as wax, alone or as a mixture. Such a wax is sold especially under the names Kester Wax K 82 P®, Hydroxypolyester K 82 P® Kester Wax K 80 P® and Kester Wax K 82 H® by the company Koster Keunen.

As microwaxes that may be used in the compositions according to the invention, mention may be made especially of carnauba microwaxes such as the product sold under the name MicroCare 350® by the company Micro Powders, synthetic microwaxes such as the product sold under the name MicroEase 114S® by the company Micro Powders, microwaxes formed from a mixture of carnauba wax and polyethylene wax, such as those sold under the names MicroCare 300® and 310® by the company Micro Powders, microwaxes formed from a mixture of carnauba wax and synthetic wax, such as the product sold under the name MicroCare 325® by the company Micro Powders, polyethylene microwaxes such as those sold under the names Micropoly 200®, 220®, 220L® and 250S® by the company Micro Powders, and polytetrafluoroethylene microwaxes such as those sold under the names Microslip 519® and 519 L® by the company Micro Powders.

d) Organophilic Clay

Mineral lipophilic gelling agents that may be mentioned include optionally modified clays such as hectorites modified with a $C_{10}$ to $C_{22}$ ammonium chloride, for instance hectorite modified with distearyldimethylammonium chloride, for instance the product sold under the name Bentone 38V® by the company Elementis.

e) Fumed Silica

Mention may also be made of optionally hydrophobic-surface-treated fumed silica with a particle size of less than 1 μm. Specifically, it is possible to chemically modify the surface of silica, via a chemical reaction that generates a reduction in the number of silanol groups present at the surface of the silica. It is especially possible to replace silanol groups with hydrophobic groups: a hydrophobic silica is then obtained. The hydrophobic groups may be:

trimethylsiloxyl groups, which are obtained especially by treating fumed silica in the presence of hexamethyldisilazane. Silicas thus treated are known as Silica silylate according to the CTFA (8th edition, 2000). They are sold, for example, under the references Aerosil R812® by the company Degussa and Cab-O-Sil TS-530® by the company Cabot, dimethylsilyloxyl or polydimethylsiloxane groups, which are especially obtained by treating fumed silica in the presence of polydimethylsiloxane or dimethyldichlorosilane. Silicas thus treated are known as Silica dimethyl silylate according to the CTFA (8th edition, 2000). They are sold, for example, under the references Aerosil R972® and Aerosil R974® by the company Degussa, and Cab-O-Sil TS-610® and Cab-O-Sil TS-720® by the company Cabot.

g) Hydrophobic Celluloses

The polymeric organic lipophilic gelling agents are, for example, cellulose derivatives such as ethylcellulose, for instance the product sold under the name Ethocel® by the company Dow Chemical; galactomannans comprising from one to six and in particular from two to four hydroxyl groups per saccharide, substituted with a saturated or unsaturated alkyl chain, for instance guar gum alkylated with $C_1$ to $C_6$ and in particular $C_1$ to $C_3$ alkyl chains, and mixtures thereof.

h) Hydrocarbon-Based Block Copolymer

The composition according to the invention may also comprise at least one hydrocarbon-based block copolymer, also referred to as a block copolymer, preferably a block copolymer that is soluble or dispersible in a liquid fatty phase.

The hydrocarbon-based block copolymer may especially be a diblock, triblock, multiblock, radial or star copolymer, or mixtures thereof.

Such hydrocarbon-based block copolymers are described in patent application US-A-2002/005 562 and in U.S. Pat. No. 5,221,534.

The copolymer may contain at least one block whose glass transition temperature is preferably less than 20° C., preferably less than or equal to 0° C., preferably less than or equal to −20° C., more preferably less than or equal to −40° C. The glass transition temperature of said block may be between −150° C. and 20° C. and especially between 100° C. and 0° C.

The hydrocarbon-based block copolymer present in the composition according to the invention is an amorphous copolymer formed by polymerization of an olefin. The olefin may especially be an ethylenically unsaturated monomer.

Examples of olefins that may be mentioned include ethylenic carbide monomers, especially containing one or two ethylenic unsaturations and containing from 2 to 5 carbon atoms, such as ethylene, propylene, butadiene, isoprene or pentadiene.

Advantageously, the hydrocarbon-based block copolymer is an amorphous block copolymer of styrene and of an olefin.

Block copolymers comprising at least one styrene block and at least one block comprising units chosen from butadiene, ethylene, propylene, butylene and isoprene or a mixture thereof are especially preferred.

According to one preferred embodiment, the hydrocarbon-based block copolymer is hydrogenated to reduce the residual ethylenic unsaturations after the polymerization of the monomers.

In particular, the hydrocarbon-based block copolymer is a copolymer, optionally hydrogenated, containing styrene blocks and ethylene/$C_3$-$C_4$ alkylene blocks.

Diblock copolymers, which are preferably hydrogenated, that may be mentioned include styrene-ethylene/propylene copolymers, styrene-ethylene/butadiene copolymers and styrene-ethylene/butylene copolymers. The diblock polymers are especially sold under the name Kraton® G1701E by the company Kraton Polymers.

Triblock copolymers, which are preferably hydrogenated, that may be mentioned include styrene-ethylene/propylene-styrene copolymers, styrene-ethylene/butadiene-styrene copolymers, styrene-ethylene/butylene-styrene copolymers, styrene-isoprene-styrene copolymers and styrene-butadiene-styrene copolymers. Triblock copolymers are especially sold under the names Kraton® G1650, Kraton® G1652, Kraton® D1101, Kraton® D1102 and Kraton® D1160 by the company Kraton Polymers.

According to one embodiment of the present invention, the hydrocarbon-based block copolymer is a styrene-ethylene/butylene-styrene triblock copolymer.

According to one preferred embodiment of the invention, a mixture of a styrene-butylene/ethylene-styrene triblock copolymer and of a styrene-ethylene/butylene diblock copolymer may especially be used, especially such as the products sold under the name Kraton® G1657M by the company Kraton Polymers.

Oil

As stated above, the structuring agents under consideration according to the invention are most generally required when the compositions that they structure comprise at least one oil whose migrating nature it is in particular sought to control so as to afford a makeup result with sharp contours on the keratin material under consideration.

A composition according to the present invention may contain at least one oil.

The term "oil" means a fatty substance that is liquid at room temperature (25° C.) and atmospheric pressure (760 mmHg, i.e. $10^5$ Pa).

According to one embodiment, a composition according to the invention may comprise an oil content ranging from 5% to 80% by weight, for example from 5% to 60% and preferably from 5% to 50% by weight, relative to the total weight of the composition.

According to another embodiment, a composition according to the present invention may comprise less than 20% by weight of fluid oil as defined below, especially less than 10% by weight or less than 5% by weight, relative to the total weight of the composition, or even is free of fluid oil.

According to yet another particular embodiment of the invention, the composition is free of any oil and especially of fluid oil and of glossy oil as defined below.

Fluid Oil

For the purposes of the invention, the term "fluid oil" denotes an oil with a molecular mass of less than 400 g/mol and in particular ranging from 100 to 390 g/mol.

This oil may be volatile or nonvolatile.

This oil may be a hydrocarbon-based or silicone oil.

For the purposes of the invention, the term "volatile oil" means an oil that is capable of evaporating on contact with the skin or the keratin fiber in less than one hour, at room temperature and atmospheric pressure. The volatile organic solvent(s) and volatile oils of the invention are volatile organic solvents and cosmetic oils that are liquid at room temperature, with a nonzero vapor pressure at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg), and more particularly ranging from 1.3 Pa to 1300 Pa (0.01 to 10 mmHg).

The term "nonvolatile oil" means an oil that remains on the skin or the keratin fiber at room temperature and atmospheric pressure for at least several hours and that especially has a vapor pressure of less than $10^{-3}$ mmHg (0.13 Pa).

A composition according to the invention may comprise less than 20 or even less than 1% of volatile oil, or else is totally free of volatile oil.

As examples of fluid oils that may be used in the invention, mention may be made of:

volatile hydrocarbon-based oils chosen from hydrocarbon-based oils containing from 8 to 16 carbon atoms, and especially branched $C_8$-$C_{16}$ alkanes, for instance $C_8$-$C_{16}$ isoalkanes of petroleum origin (also known as isoparaffins), for instance isododecane (also known as 2,2,4,4,6-pentamethylheptane), isodecane and isohexadecane, for example the oils sold under the trade names Isopar or Permethyl, branched $C_8$-$C_{16}$ esters and isohexyl neopentanoate, and mixtures thereof. Other volatile hydrocarbon-based oils, for instance petroleum distillates, especially those sold under the name Shell Solt by the company Shell, may also be used;

volatile silicones, for instance volatile linear or cyclic silicone oils, especially those with a viscosity ≤8 centistokes ($8 \times 10^{-6}$ m$^2$/s) and especially containing from 2 to 6 silicon atoms, these silicones optionally comprising alkyl or alkoxy groups containing from 1 to 10 carbon atoms. As volatile silicone oils that may be used in the invention, mention may be made especially of octamethylcyclotetrasiloxane, heptamethyloctyltrisiloxane, hexamethyldisiloxane, octamethyltrisiloxane and decamethyltetrasiloxane;

synthetic esters, especially of fatty acids, for instance the oils of formula $R_1COOR_2$ in which $R_1$ represents a linear or branched higher fatty acid residue containing from 1 to 30 carbon atoms and $R_2$ represents a hydrocarbon-based chain, which is especially branched, containing from 1 to 30 carbon atoms, with $R_1+R_2<30$, for instance purcellin oil (cetostearyl octanoate), isononyl isononanoate, isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate; alcohol or polyalcohol octanoates, decanoates or ricinoleates, for instance propylene glycol dioctanoate; hydroxylated esters, for instance isostearyl lactate, octyl hydroxystearate, octyldodecyl hydroxystearate, diisostearyl malate, triisocetyl citrate, and fatty alcohol heptanoates, octanoates or decanoates; polyol esters, for instance propylene glycol dioctanoate, neopentyl glycol diheptanoate or diethylene glycol diisononanoate;

fatty alcohols that are liquid at room temperature, with a branched and/or unsaturated carbon-based chain containing from 8 to 26 carbon atoms, for instance oleyl alcohol, linoleyl alcohol, linolenyl alcohol, isostearyl alcohol or octyldodecanol as sold under the commercial reference Eutanol G® by the company Cognis;

higher fatty acids such as oleic acid, linoleic acid or linolenic acid;

carbonates;

acetates;

citrates;

silicone oils such as polydimethylsiloxanes (PDMS); and mixtures thereof.

Glossy Oil

A composition according to the invention may contain at least one glossy oil.

According to the invention, the term "glossy oil" more specifically means a hydrocarbon-based or silicone oil with a molecular mass of greater than 400 g/mol, or even 500 g/mol and especially 650 g/mol. In particular, this glossy oil may have a molar mass ranging from 400 to 10 000 g/mol, in particular from 650 to 10 000 g/mol and more particularly ranging from 650 to 5000 g/mol.

In particular, a composition comprises a sufficient amount of glossy oil(s) to afford at least makeup performance of gloss type.

A composition according to the invention may comprise a content of glossy oil(s) ranging from 0 to 20%, for example from 0 to 10% by weight and preferably from 0 to 5% by weight relative to the total weight of the composition.

This glossy oil may be polar or apolar.

This glossy oil is advantageously an oil chosen from oils of high molar mass in particular having a molar mass ranging from 500 to 10 000 g/mol, in particular from 500 to 8000 g/mol and more particularly from 550 to 7500 g/mol.

Preferably, the glossy oil has a refractive index of greater than or equal to 1.45 and especially ranging from 1.45 to 1.6.

The glossy oil is preferably a nonvolatile oil.

Advantageously, a hydrocarbon-based glossy oil that may be used in the present invention may be chosen from:

lipophilic polymers such as:

polybutylenes such as Indopol H-100 (of molar mass MW=965 g/mol), Indopol H-300 (MW=1340 g/mol) or Indopol H-1500 (MW=2160 g/mol) sold or manufactured by the company Amoco, hydrogenated polyisobutylenes such as Panalane H-300 E sold or manufactured by Amoco (MW=1340 g/mol), Viseal 20000 sold or manufactured by the company Synteal (MW=6000 g/mol) and Rewopal PIB 1000 sold or manufactured by the company Witco (MW=1000 g/mol), polydecenes and hydrogenated polydecenes such as: Puresyn 10 (MW=723 g/mol) and Puresyn 150 (MW=9200 g/mol) sold or manufactured by the company Mobil Chemicals, vinylpyrrolidone copolymers such as: the vinylpyrrolidone/1-hexadecene copolymer Antaron V-216 sold or manufactured by the company ISP (MW=7300 g/mol), esters such as:

linear fatty acid esters with a total carbon number ranging from 35 to 70, for instance pentaerythrityl tetrapelargonate (MW=697 g/mol), hydroxylated esters such as polyglyceryl-2-triisostearate (MW=965 g/mol), triisocetyl citrate (MW=864 g/mol), diisostearyl malate (MW=639 g/mol), aromatic esters such as tridecyl trimellitate (MW=757 g/mol), $C_{24}$-$C_{28}$ esters of branched fatty alcohols or fatty acids such as those described in patent application EP-A-0 955 039, and especially triisoarachidyl citrate (MW=1033.76 g/mol), pentaerythrityl tetraisononanoate (MW=697 g/mol), glyceryl triisostearate (MM=891 g/mol), glyceryl tris(2-decyl)tetradecanoate (MW=1143 g/mol), pentaerythrityl tetraisostearate (MW=1202 g/mol), polyglyceryl-2 tetraisostearate (MW=1232 g/mol) or pentaerythrityl tetrakis(2-decyl)tetradecanoate (MW=1538 g/mol), a polyester resulting from the esterification of at least one hydroxylated carboxylic acid triglyceride with an aliphatic monocarboxylic acid and with an aliphatic dicarboxylic acid, which is optionally unsaturated, such as the castor oil of succinic acid and of isostearic acid sold under the reference Zenigloss by Zenitech, esters of a diol dimer and of a diacid dimer of general formula:

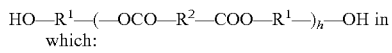

which:

$R^1$ represents a diol dimer obtained by hydrogenation of dilinoleic diacid, $R^2$ represents a hydrogenated dilinoleic diacid residue, and h represents an integer ranging from 1 to 9, especially the esters of dilinoleic diacids and of dilinoleyl diol dimers sold by the company Nippon Fine Chemical under the trade names Lusplan DD-DA5® and DD-DA7®, oils of plant origin, for instance sesame oil (MW=820 g/mol), and mixtures thereof.

The hydrocarbon-based glossy oil may also be a triglyceride oligomer of a hydroxylated fatty acid and of a saturated diacid.

Such an oligomer is obtained by reacting a hydroxylated fatty acid triglyceride (such as hydrogenated castor oil) and a saturated diacid.

According to the invention, the diacid is said to be saturated when the hydrocarbon-based chain of which it is formed does not comprise any unsaturation, i.e. any carbon-carbon double bonds. The term "diacid" means a hydrocarbon-based compound comprising two carboxyl functions —COOH. The diacid may be a single diacid or a mixture of several diacids.

Similarly, for the purposes of the invention, the oligomer may be a mixture of several oligomers.

Among the saturated diacids that may be used, mention may be made of sebacic acid (or 1,10-decanedioic acid), succinic acid, adipic acid, azelaic acid, octadecamethylenedicarboxylic acid and eicosadicarboxylic acid.

More particularly, the oligomer may be an oligoester in which the monomers are represented by the triglyceride (A) and diacid (B) formulae below:

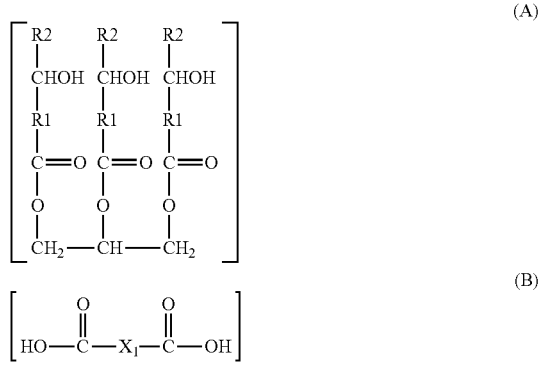

in which:
$R_1$ represents a saturated or unsaturated, linear or branched alkylene group containing, for example, from 1 to 18 carbon atoms, and $R_2$ represents a saturated or unsaturated, linear or branched alkyl group containing, for example, from 1 to 12 carbon atoms;
$R_1$ preferably represents a group —$(CH_2)_n$—, in which n may range from 1 to 20 and especially from 3 to 16, for example from 6 to 12;
$R_2$ preferably represents a group —$(CH_2)_m$—$CH_3$, in which m may range from 0 to 11 and especially from 2 to 11, for example from 3 to 9.

According to one embodiment, n=10 and m=5, and the group

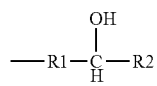

represents the alkyl residue of 12-hydroxystearic acid (which is a major component of hydrogenated castor oil);
$X_1$ is a linear or branched alkylene group, for instance a linear alkylene group —$(CH_2)_x$— in which x may range from 1 to 30 and especially from 3 to 15.

When the diacid is sebacic acid, x is equal to 8.

The average degree of polymerization of the oligomer may range between 3 and 12.

The oligoester of hydrogenated castor oil and of sebacic acid is sold especially by the company Croda under various names depending on the degree of polymerization.

Among the oligoesters formed from hydrogenated castor oil and sebacic acid, the one with a degree of polymerization of about 4.6 is available under the trade name Cromadol CWS-5 and that with a degree of polymerization of about 9.5 is available under, the trade name Cromadol CWS-10, sold by Croda Japan K.K.

The oligomer of hydrogenated castor oil and of sebacic acid sold under the name Crodabond-CSA (MW=3500) by the company Croda is also mentioned.

The glossy oil may also be an oil chosen from silicone oils, for instance polydimethylsiloxanes (PDMS); phenyl silicones such as phenyl trimethicones (such as the phenyl trimethicone sold under the trade name DC556 by Dow Corning), phenyl dimethicones, phenyl trimethylsiloxy diphenyl siloxanes, diphenyl dimethicones, diphenyl methyldiphenyl trisiloxane, trimethyl pentaphenyl trisiloxane (especially 1,3, 5-trimethyl-1,1,3,5,5-pentaphenyltrisiloxane sold under the name PH-1555 HRI by Dow Corning) and mixtures thereof.

It is preferably a hydrocarbon-based oil.

Fatty Phase

A composition according to the invention comprises at least one fatty phase, for example in a proportion of at least 50% by weight, in particular at least 60% by weight, especially at least 70% by weight, or even at least 80% by weight relative to the total weight of the composition.

This phase may contain, besides at least one oil as defined above, at least one pasty compound.

Pasty Compounds

For the purposes of the present invention, the term "pasty compound" is intended to denote a lipophilic fatty compound that undergoes a reversible solid/liquid change of state, that has anisotropic crystal organization in the solid state, and that comprises, at a temperature of 23° C., a liquid fraction and a solid fraction.

In other words, the starting melting point of the pasty compound is less than 23° C. The liquid fraction of the pasty compound measured at 23° C. may represent 9% to 97% by weight of the compound. This liquid fraction at 23° C. preferably represents between 15% and 85% and more preferably between 40% and 85% by weight.

The liquid fraction by weight of the pasty compound at 23° C. is equal to the ratio of the heat of fusion consumed at 23° C. to the heat of fusion of the pasty compound.

The heat of fusion of the pasty compound is the heat consumed by the compound to change from the solid state to the liquid state. The pasty compound is said to be in the solid state when all of its mass is in solid form. The pasty compound is said to be in the liquid state when all of its mass is in liquid form.

The heat of fusion of the pasty compound is equal to the area under the curve of the thermogram obtained using a differential scanning calorimeter (DSC), such as the calorimeter sold under the name MDSC 2920 by the company TA Instruments, with a temperature rise of 5 or 10° C. per minute, according to standard ISO 11357-3:1999. The heat of fusion of the pasty compound is the amount of energy required to make the compound change from the solid state to the liquid state. It is expressed in J/g.

The heat of fusion consumed at 23° C. is the amount of energy absorbed by the sample to change from the solid state to the state that it has at 23° C., consisting of a liquid fraction and a solid fraction.

The liquid fraction of the pasty compound, measured at 32° C., preferably represents from 30% to 100% by weight of the compound, preferably from 50% to 100% and more preferably from 60% to 100% by weight of the compound. When the liquid fraction of the pasty compound measured at 32° C.

is equal to 100%, the temperature of the end of the melting range of the pasty compound is less than or equal to 32° C.

The liquid fraction of the pasty compound measured at 32° C. is equal to the ratio of the heat of fusion consumed at 32° C. to the heat of fusion of the pasty compound. The heat of fusion consumed at 32° C. is calculated in the same manner as the heat of fusion consumed at 23° C.

The pasty compound is preferably chosen from synthetic compounds and compounds of plant origin. A pasty compound may be obtained by synthesis starting from starting materials of plant origin.

The pasty compound may be advantageously chosen from:
i) lanolin and derivatives thereof,
ii) polymer or nonpolymer silicone compounds,
iii) polymer or nonpolymer fluoro compounds,
iv) vinyl polymers, especially:
  olefin homopolymers and olefin copolymers,
  hydrogenated diene homopolymers and copolymers,
  linear or branched oligomers, which are homopolymers or copolymers of alkyl (meth)acrylates preferably containing a $C_8$-$C_{30}$ alkyl group,
  vinylpyrrolidone/eicosene copolymers (INCI name VP/eicosene copolymer), for example the product sold by the company ISP under the trade name Ganex V220F®,
  oligomers, which are homopolymers and copolymers of vinyl ethers containing $C_8$-$C_{30}$ alkyl groups,
v) liposoluble polyethers resulting from polyetherification between one or more $C_2$-$C_{100}$ and preferably $C_2$-$C_{50}$ diols,
vi) esters,
vii) and mixtures thereof.
  Among the esters, the following are especially preferred:
  esters of a glycerol oligomer, especially diglycerol esters, in particular condensates of adipic acid and of glycerol, for which some of the hydroxyl groups of the glycerols have reacted with a mixture of fatty acids such as stearic acid, capric acid, stearic acid and isostearic acid, and 12-hydroxystearic acid, especially such as bis(diglyceryl)poly(2-acyladipate), especially the product sold under the brand name Softisan 649° by the company Sasol,
  arachidyl propionate sold under the brand name Waxenol 801 by Alzo,
  phytosterol esters,
  fatty acid triglycerides and derivatives thereof,
  pentaerythritol esters,
  noncrosslinked polyesters resulting from polycondensation between a linear or branched $C_4$-$C_{50}$ dicarboxylic acid or polycarboxylic acid and a $C_2$-$C_{50}$ diol or polyol,
  aliphatic esters of an ester resulting from the esterification of an aliphatic hydroxycarboxylic acid ester with an aliphatic carboxylic acid,
  esters resulting from the esterification of an aliphatic acid and a hydroxylated aliphatic ester. These esters may result from the esterification a) of a monocarboxylic or polycarboxylic aliphatic acid, and b) of a hydroxylated aliphatic ester, especially a hydroxycarboxylic acid ester,
  esters of diol dimer and of diacid dimer, where appropriate esterified on their free alcohol or acid function(s) with acid or alcohol radicals, such as bis-behenyl/isostearyl/phytosteryl dimer dilinoleyl sold especially under the trade name Plandool-G® by the company Nippon Fine Chemical,
  and mixtures thereof.

Among the pasty compounds, bis-behenyl/isostearyl/phytosteryl dimer dilinoleyl, bis(diglyceryl)poly(2-acyladipate), hydrogenated castor oil dimer dilinoleate, for example Risocast DA-14 sold by Kokyu Alcohol Kogyo, and hydrogenated castor oil isostearate, for example Salacos HCIS (V-L) sold by Nisshin Oil, or a mixture thereof, will preferably be chosen.

The content of pasty compound may range from 5% to 90% by weight, especially from 5% to 50% by weight, or even, in certain embodiments, from 5% to 35% by weight, relative to the total weight of the composition.

Besides the abovementioned compounds, a composition according to the invention may also comprise other compounds especially as defined below. It is understood that the amount of these additional compounds may be adjusted by a person skilled in the art so as not to harm the desired effect in the context of the present invention.

The compositions may also comprise at least one polymer comprising at least two groups capable of interacting via hydrogen bonding.

Polymer Comprising at Least Two Groups Capable of Interacting Via Hydrogen Bonds According to one particular embodiment, the polymer comprising at least two groups capable of interacting via hydrogen bonding is present in the composition in a total content ranging from 0.5% to 50% by weight relative to the total weight of the composition, preferably ranging from 5% to 50% by weight and better still ranging from 8% to 45% by weight, for example ranging from 10% to 40% by weight, relative to the total weight of said composition.

According to the invention, the polymer comprising at least two groups capable of interacting via hydrogen bonding may belong to the following two families:
1) polymers comprising at least two groups capable of establishing hydrogen interactions, these two groups being located in the polymer chain, and/or
2) polymers comprising at least two groups capable of establishing hydrogen interactions, these two groups being located on grafts or branches.

For the purposes of the invention, the term "polymer" means a compound containing at least two repeating units and preferably at least three repeating units.

For the purposes of the invention, the term "repeating units" means a unit comprising from 2 to 80 carbon atoms and preferably from 2 to 60 carbon atoms, bearing hydrogen atoms and optionally oxygen atoms, which may be linear, branched or cyclic, and saturated or unsaturated. These units each also comprise one or more nonpendent heteroatoms that are in the polymer backbone. These heteroatoms are chosen from nitrogen, sulfur, phosphorus and silicon atoms and combinations thereof, optionally combined with one or more oxygen atoms.

Preferably, these groups are chosen from amide, sulfonamide, carbamate, thiocarbamate, urea, urethane, thiourea, oxamido, guanidino and biguanidino groups, and combinations thereof.

As polymers comprising at least two groups capable of interacting via hydrogen bonding, examples that may be mentioned include:
  polymers with a weight-average molecular mass of less than 100 000, comprising a) a polymer backbone with hydrocarbon-based repeating units containing at least one heteroatom, and optionally b) at least one pendent fatty chain and/or at least one terminal fatty chain, optionally functionalized, containing from 6 to 120 carbon atoms and being linked to these hydrocarbon-based units, as described in patent applications WO-A-02/056 847 and WO-A-02/47619, the content of which is incorporated herein by reference; in particular polyamide resins (especially comprising alkyl groups containing from 12 to 22 carbon atoms) such as those described in U.S. Pat. No. 5,783,657, the content of which is incorporated herein by reference, silicone polyamide resins as described in patent application EP-A-1 266 647, and in the French patent application filed under No. 0 216 039, the content of which is incorporated herein by reference, organopolysiloxanes comprising at least one carboxyl group, and preferably organopolysiloxanes comprising at least two carboxyl groups, per unit.

Such polymers comprising at least two groups capable of interacting via hydrogen bonding are described especially in patent application EP-A-1 400 234, the content of which is incorporated herein by reference, and are described in greater detail hereinbelow.

Silicone Polymer

According to a first embodiment of the invention, the polymer comprising at least two groups capable of interacting via hydrogen bonding is a silicone polyamide.

The silicone polyamides are preferably solid at room temperature (25° C.) and atmospheric pressure (760 mmHg).

The silicone polyamides of the composition of the invention may be polymers of the polyorganosiloxane type, for instance those described in documents U.S. Pat. No. 5,874,069, U.S. Pat. No. 5,919,441, U.S. Pat. No. 6,051,216 and U.S. Pat. No. 5,981,680. According to the invention, the silicone polymers may belong to the following two families:

(1) polyorganosiloxanes comprising at least two amide groups, these two groups being located in the polymer chain, and/or (2) polyorganosiloxanes comprising at least two amide groups, these two groups being located on grafts or branches.

A) According to a first variant, the silicone polymers are polyorganosiloxanes as defined above in which the amide units are located in the polymer chain.

The silicone polyamides may more particularly be polymers comprising at least one unit corresponding to the general formula I:

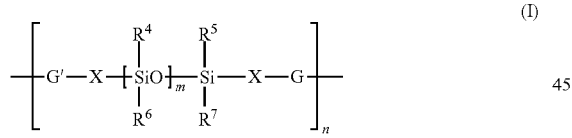

in which:
1) G' represents C(O) when G represents —C(O)—NH—Y—NH—, and G' represents —NH— when G represents —NH—C(O)—Y—C(O)—,
2) $R^4$, $R^5$, $R^6$ and $R^7$, which may be identical or different, represent a group chosen from:
   linear, branched or cyclic, saturated or unsaturated, $C_1$-$C_{40}$ hydrocarbon-based groups, possibly containing in their chain one or more oxygen, sulfur and/or nitrogen atoms, and possibly being partially or totally substituted with fluorine atoms,
   $C_6$-$C_{10}$ aryl groups, optionally substituted with one or more $C_1$-$C_4$ alkyl groups,
   polyorganosiloxane chains possibly containing one or more oxygen, sulfur and/or nitrogen atoms;
3) the groups X, which may be identical or different, represent a linear or branched $C_1$-$C_{30}$ alkylenediyl group, possibly containing in its chain one or more oxygen and/or nitrogen atoms;

4) Y is a saturated or unsaturated, $C_{10}$-$C_{50}$ linear or branched divalent alkylene, arylene, cycloalkylene, alkylarylene or arylalkylene group, possibly comprising one or more oxygen, sulfur and/or nitrogen atoms, and/or bearing as substituent one of the following atoms or groups of atoms: fluorine, hydroxyl, $C_3$-$C_8$ cycloalkyl, $C_1$-$C_{40}$ alkyl, $C_5$-$C_{10}$ aryl, phenyl optionally substituted with 1 to 3 $C_1$-$C_3$ alkyl, $C_1$-$C_3$ hydroxyalkyl and $C_1$-$C_6$ aminoalkyl groups; or 5) Y represents a group corresponding to the formula:

in which
T represents a linear or branched, saturated or unsaturated, $C_3$-$C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and $R^8$ represents a linear or branched $C_{10}$-$C_{50}$ alkyl group or a polyorganosiloxane chain, possibly comprising one or more ester, amide, urethane, thiocarbamate, urea, thiourea and/or sulfonamide groups, which may possibly be linked to another chain of the polymer;

6) n is an integer ranging from 2 to 500 and preferably from 2 to 200, and m is an integer ranging from 1 to 1000, preferably from 1 to 700 and better still from 6 to 200.

According to one embodiment of the invention, 80% of the groups $R^4$, $R^5$, $R^6$ and $R^7$ of the polymer are preferably chosen from methyl, ethyl, phenyl and 3,3,3-trifluoropropyl groups. According to another embodiment, 80% of the groups $R^4$, $R^5$, $R^6$ and $R^7$ of the polymer are methyl groups.

Preferably, Y represents a group chosen from:
a) linear $C_1$ to $C_{20}$ and preferably $C_1$ to $C_{10}$ alkylene groups,
b) $C_{30}$ to $C_{56}$ branched alkylene groups possibly comprising rings and unconjugated unsaturations,
c) $C_5$-$C_6$ cycloalkylene groups,
d) phenylene groups optionally substituted with one or more $C_1$ to $C_{40}$ alkyl groups,
e) $C_1$ to $C_{20}$ alkylene groups comprising from 1 to 5 amide groups,
f) $C_1$ to $C_{20}$ alkylene groups comprising one or more substituents chosen from hydroxyl, $C_3$ to $C_8$ cycloalkane, $C_1$ to $C_3$ hydroxyalkyl and $C_1$ to $C_6$ alkylamine groups,
g) polyorganosiloxane chains of formula:

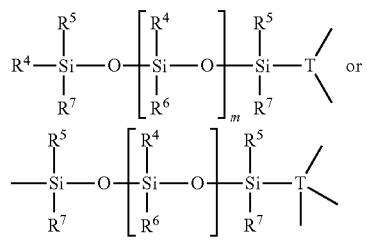

in which $R^4$, $R^5$, $R^6$, $R^7$, T and m are as defined above.

B) According to the second variant, the silicone polyamides may be polymers comprising at least one unit corresponding to formula (II):

$$\left[\begin{array}{c} R^4 \\ | \\ -Si-O- \\ | \\ R^6 \end{array}\right]_{m_1} \left[\begin{array}{c} R^{11} \\ | \\ Si-O- \\ | \\ R^{10} \end{array}\right]_{m_2} \quad (II)$$

in which
- $R^4$ and $R^6$, which may be identical or different, are as defined above for formula (I),
- $R^{10}$ represents a group as defined above for $R^4$ and $R^6$, or represents a group of formula —X-G"-$R^{12}$ in which X is as defined above for formula (I) and $R^{12}$ represents a hydrogen atom or a linear, branched or cyclic, saturated or unsaturated, $C_1$-$C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$-$C_4$ alkyl groups,
- and G" represents —C(O)NH— and —HN—C(O)—,
- $R^{11}$ represents a group of formula —X-G"—$R^{12}$ in which X, G" and $R^{12}$ are as defined above,
- $m_1$ is an integer ranging from 1 to 998, and
- $m_2$ is an integer ranging from 2 to 500.

According to the invention, the silicone polymer may be a homopolymer, i.e. a polymer comprising several identical units, in particular units of formula (I) or of formula (II).

According to the invention, it is also possible to use a polymer consisting of a copolymer comprising several different units of formula (I), i.e. a polymer in which at least one of the groups $R^4$, $R^5$, $R^6$, $R^7$, X, G, Y, m and n is different in one of the units. The copolymer may also be formed from several units of formula (II), in which at least one of the groups $R^4$, $R^6$, $R^{10}$, $R^{11}$, $m_1$ and $m_2$ is different in at least one of the units.

It is also possible to use a polymer comprising at least one unit of formula (I) and at least one unit of formula (II), the units of formula (I) and the units of formula (II) possibly being identical to or different than each other.

According to one variant of the invention, it is also possible to use a polymer furthermore comprising at least one hydrocarbon-based unit comprising two amide groups, chosen from ester, amide, sulfonamide, carbamate, thiocarbamate, urea, urethane, thiourea, oxamido, guanidine and biguanidino groups, and combinations thereof.

These copolymers may be block polymers or grafted polymers.

In formulae (I) and (II), the alkylene group representing X or Y can optionally contain in its alkylene part at least one of the following components:
1) one to five amide, urea, urethane or carbamate groups,
2) a $C_s$ or $C_6$ cycloalkyl group, and
3) a phenylene group optionally substituted with 1 to 3 identical or different $C_1$-$C_3$ alkyl groups.

In formulae (I) and (II), the alkylene groups may also be substituted with at least one component chosen from the group consisting of
- a hydroxyl group,
- a $C_3$ to $C_8$ cycloalkyl group,
- one to three $C_1$ to $C_{40}$ alkyl groups,
- a phenyl group optionally substituted with one to three $C_1$ to $C_3$ alkyl groups,
- a $C_1$ to $C_3$ hydroxyalkyl group, and
- a $C_1$ to $C_6$ aminoalkyl group.

In these formulae (I) and (II), Y may also represent:

$$R^8-T\diagdown$$

in which $R^8$ represents a polyorganosiloxane chain and T represents a group of formula:

$$-(CH_2)_a-\underset{\underset{|}{(CH_2)_c}}{\overset{\overset{R^{13}}{|}}{C}}-(CH_2)_b- \quad \text{ou}$$

$$-(CH_2)_a-\underset{\underset{|}{(CH_2)_c}}{N}-(CH_2)_b-$$

in which a, b and c are, independently, integers ranging from 1 to 10, and $R^{13}$ is a hydrogen atom or a group such as those defined for $R^4$, $R^5$, $R^6$ and $R^7$.

In formulae (I) and (II), $R^4$, $R^5$, $R^6$ and $R^7$ preferably represent, independently, a linear or branched $C_1$ to $C_{40}$ alkyl group, preferably a $CH_3$, $C_2H_5$, n-$C_3H_7$ or isopropyl group, a polyorganosiloxane chain or a phenyl group optionally substituted with one to three methyl or ethyl groups.

As has been seen previously, the polymer may comprise identical or different units of formula (I) or (II).

Thus, the polymer may be a polyamide containing several units of formula (I) or (II) of different lengths, i.e. a polyamide corresponding to formula (III):

$$\left[-C(O)-X-\left[SiO\right]_{m_1}-Si-X-C(O)-NH-Y-NH-\right]_n \left[-C(O)-X-\left[SiO\right]_{m_2}-Si-X-C(O)-NH-Y-NH-\right]_p \quad (III)$$

in which X, Y, n and $R^4$ to $R^7$ have the meanings given above, $m_1$ and $m_2$, which are different, are chosen in the range from 1 to 1000, and p is an integer ranging from 2 to 300.

In this formula, the units may be structured to form either a block copolymer, or a random copolymer or an alternating copolymer. In this copolymer, the units may be not only of different lengths, but also of different chemical structures, for example containing different groups Y. In this case, the polymer may correspond to formula IV:

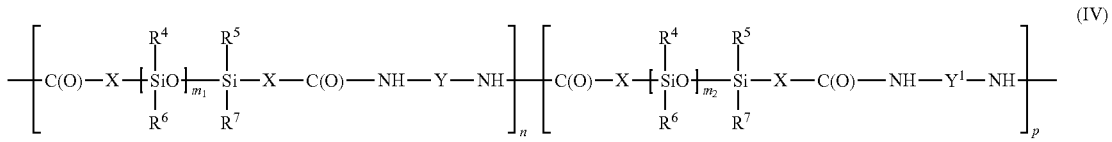

in which $R^4$ to $R^7$, X, Y, $m_1$, $m_2$, n and p have the meanings given above and $Y^1$ is different than Y but chosen from the groups defined for Y. As previously, the various units may be structured to form either a block copolymer, or a random copolymer or an alternating copolymer.

In this first embodiment of the invention, the silicone polymer may also be formed from a grafted copolymer. Thus, the polyamide containing silicone units may be grafted and optionally crosslinked with silicone chains containing amide groups. Such polymers may be synthesized with trifunctional amines.

According to the invention, as has been seen previously, the siloxane units may be in the main chain or backbone of the polymer, but they may also be present in grafted or pendent chains. In the main chain, the siloxane units may be in the form of segments as described above. In the pendent or grafted chains, the siloxane units may appear individually or in segments.

According to one embodiment variant of the invention, a copolymer of silicone polyamide and of hydrocarbon-based polyamide, or a copolymer comprising units of formula (I) or (II) and hydrocarbon-based polyamide units, may be used. In this case, the polyamide-silicone units may be located at the ends of the hydrocarbon-based polyamide.

Advantageously, the composition comprises at least one polyamide/polydimethylsiloxane polymer, especially a polymer of general formula (I) with an index m of greater than 50, in particular greater than 75, especially between 50 and 200, for example of about 100.

Advantageously, the silicone polyamide of formula (I) has a weight-average molecular mass ranging from 10 000 to 500 000 g/mol.

More preferably, X and Y independently represent a group chosen from linear $C_1$ to $C_{20}$ and preferably $C_1$ to $C_{10}$ alkylene groups.

As examples of polymers that may be used, mention may be made of one of the silicone polyamides obtained in accordance with Examples 1 to 3 of document U.S. Pat. No. 5,981,680, such as the product sold under the reference DC 2-8179 by Dow Corning.

According to one embodiment variant of the invention, the polymer consists of a homopolymer or copolymer comprising urethane or urea groups. These polymers are described in detail in patent application WO 2003/106 614.

The first composition may contain, in place of the silicone polyamide, a polyorganosiloxane polymer containing two or more urethane and/or urea groups, either in the backbone of the polymer or on side chains or as pendent groups.

The polymers comprising at least two urethane and/or urea groups in the backbone may be polymers comprising at least one unit corresponding to the following formula:

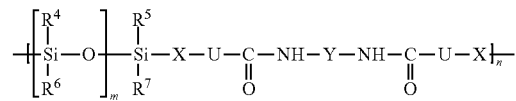

in which $R^4$, $R^5$, $R^6$, $R^7$, X, Y, m and n have the meanings given above for formula (I), and U represents —O— or —NH—, such that:

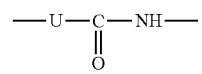

corresponds to a urethane or urea group.

In this formula, Y may be a linear or branched $C_1$-$C_{40}$ alkylene group, optionally substituted with a $C_1$-$C_{15}$ alkyl group or a $C_6$-$C_{10}$ aryl group. Preferably, a —$(CH_2)_6$— group is used.

The polymer constituting the silicone polymer may be formed from silicone-urethane and/or silicone-urea units of different length and/or constitution, and may be in the form of block, sequenced or statistical (random) copolymers.

As in the case of the silicone polyamides of formula (I), (II) or (III), silicone polyurethanes or polyureas having units of different length and structure, in particular units of different lengths via the number of silicone units, may be used in the invention.

The polymers and copolymers used in the composition of the invention advantageously have a transition temperature from the solid state to the liquid state ranging from 45° C. to 190° C. Preferably, they have a transition temperature from the solid state to the liquid state ranging from 70 to 130° C. and better still from 80° C. to 105° C.

The silicone polyamide may be present in the first composition in a total content ranging from 0.5% to 70% by weight relative to the total weight of the composition, preferably ranging from 5% to 50% by weight, better still ranging from 8% to 45% by weight and preferably ranging from 10% to 40% by weight relative to the total weight of said composition.

Hydrocarbon-Based Polymer

According to a second embodiment of the invention, the polymer comprising at least two groups capable of interacting via hydrogen bonding is a polymer with a weight-average molecular mass of less than 100 000, comprising a) a polymer backbone with hydrocarbon-based repeating units containing at least one heteroatom, and optionally b) at least one pendent fatty chain and/or at least one terminal fatty chain, optionally functionalized, containing from 6 to 120 carbon atoms and being linked to these hydrocarbon-based units, as described in patent applications WO-A-02/056 847 and WO-A-02/47619, the content of which is incorporated herein by reference; in particular polyamide resins (especially comprising alkyl groups containing from 12 to 22 carbon atoms) such as those described in U.S. Pat. No. 5,783,657, the content of which is incorporated herein by reference.

The polymer according to the invention is an undeformable solid at room temperature (25° C.).

For the purposes of the invention, the term "functionalized chains" means an alkyl chain comprising one or more functional groups or reagents chosen especially from hydroxyl, ether, oxyalkylene or polyoxyalkylene, halogen, including fluoro or perfluoro groups, and ester groups. In addition, the hydrogen atoms of one or more fatty chains may be at least partially replaced with fluorine atoms.

Preferably, the hydrocarbon-based repeating units comprise at least one nitrogen atom, in particular a nonpendent nitrogen atom. These units also advantageously comprise a carbonyl group.

The units containing a heteroatom are, in particular, amide units forming a backbone of the polyamide type, carbamate and/or urea units forming a polyurethane, polyurea and/or polyurea-urethane backbone. These units are preferably amide units. The pendent chains are advantageously linked directly to at least one of the heteroatoms of the polymer backbone.

Between the hydrocarbon-based units, this polymer may comprise silicone units or oxyalkylene units.

In addition, this polymer of the composition of the invention advantageously comprises from 40% to 98% of fatty chains relative to the total number of units containing a heteroatom and of fatty chains, and better still from 50% to 95%. The nature and proportion of the units containing a heteroatom depends on the nature of the fatty phase and is, in particular, similar to the polar nature of the fatty phase. Thus, the more the units containing a heteroatom are polar and in high proportion in the first polymer, which corresponds to the presence of several heteroatoms, the greater the affinity of the first polymer for polar oils. On the other hand, the less polar or even apolar the units containing a heteroatom or the lower their proportion, the greater the affinity of the first polymer for apolar oils.

This polymer is advantageously a polyamide. Thus, a subject of the invention is also a composition containing, in a cosmetically acceptable medium, at least one polyamide polymer with a weight-average molecular mass of less than 100 000, comprising a) a polymer backbone containing amide repeating units, and b) optionally at least one pendent fatty chain and/or at least one terminal chain, which may be functionalized, containing from 8 to 120 carbon atoms and being linked to these amide units.

The pendent fatty chains are preferably linked to at least one of the nitrogen atoms of the amide units of this polymer.

In particular, the fatty chains of this polyamide represent from 40% to 98% of the total number of amide units and of fatty chains, and better still from 50% to 95%.

Advantageously, this polymer, and in particular this polyamide, of the composition according to the invention has a weight-average molecular mass of less than 100 000 (especially ranging from 1000 to 100 000), in particular less than 50 000 (especially ranging from 1000 to 50 000) and more particularly ranging from 1000 to 30 000, preferably from 2000 to 20 000 and better still from 2000 to 10 000.

This polymer, and in particular this polyamide, is insoluble in water, especially at 25° C. In particular, it contains no ionic groups.

As preferred polymers that may be used in the invention, mention may be made of polyamides branched with pendent fatty chains and/or terminal fatty chains containing from 6 to 120 carbon atoms and better still from 8 to 120 and in particular from 12 to 68 carbon atoms, each terminal fatty chain being linked to the polyamide backbone via at least one bonding group, in particular an ester. These polymers preferably comprise a fatty chain at each end of the polymer backbone and in particular of the polyamide backbone. Other bonding groups which may be mentioned are ether, amine, urea, urethane, thioester, thiourea and thiourethane groups.

These polymers are preferably polymers resulting from a polycondensation between a dicarboxylic acid containing at least 32 carbon atoms (in particular containing from to 44 carbon atoms) and an amine chosen from diamines containing at least 2 carbon atoms (in particular from 2 to 36 carbon atoms) and triamines containing at least 2 carbon atoms (in particular from 2 to 36 carbon atoms). The diacid is preferably a dimer of a fatty acid containing ethylenic unsaturation containing at least 16 carbon atoms, preferably from 16 to 24 carbon atoms, for instance oleic acid, linoleic acid or linolenic acid. The diamine is preferably ethylenediamine, hexylenediamine or hexamethylenediamine. The triamine is, for example, ethylenetriamine. For the polymers comprising one or two terminal carboxylic acid groups, it is advantageous to esterify them with a monoalcohol containing at least four carbon atoms, preferably from 10 to 36 carbon atoms, better still from 12 to 24 and even better from 16 to 24, for example 18 carbon atoms.

These polymers are more especially those disclosed in document U.S. Pat. No. 5,783,657 from the company Union Camp. Each of these polymers in particular satisfies formula (I) below:

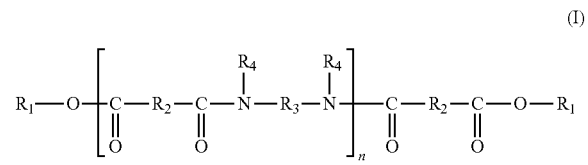

in which n denotes a number of amide units such that the number of ester groups represents from 10% to 50% of the total number of ester and amide groups; $R^1$ is, independently in each case, an alkyl or alkenyl group containing at least 4 carbon atoms and in particular from 4 to 24 carbon atoms; $R^2$ represents, independently in each case, a $C_4$ to $C_{42}$ hydrocarbon-based group, on condition that 50% of the groups $R^2$ represent a $C_{30}$ to $C_{42}$ hydrocarbon-based group; $R^3$ represents, independently in each case, an organic group containing at least 2 carbon atoms, hydrogen atoms and optionally one or more oxygen or nitrogen atoms; and $R^4$ represents, independently in each case, a hydrogen atom, a $C_1$ to $C_{10}$ alkyl group or a direct bond to $R^3$ or to another $R^4$, such that the nitrogen atom to which $R^3$ and $R^4$ are both attached forms part of a heterocyclic structure defined by $R^4$—N—$R^3$, with at least 50% of the groups $R^4$ representing a hydrogen atom.

In the particular case of formula (I), the terminal fatty chains that are optionally functionalized for the purposes of the invention are terminal chains linked to the last heteroatom, in this case nitrogen, of the polyamide backbone.

In particular, the ester groups of formula (I), which form part of the terminal and/or pendent fatty chains for the purposes of the invention, represent from 15% to 40% of the total number of ester and amide groups and better still from 20% to 35%. Furthermore, n is advantageously an integer ranging from 1 to 5 and better still greater than 2. Preferably, $R^1$ is a $C_{12}$ to $C_{22}$ and preferably $C_{16}$ to $C_{22}$ alkyl group. Advantageously, $R^2$ can be a $C_{10}$ to $C_{42}$ hydrocarbon-based (alkylene) group. Preferably, at least 50% and better still at least 75% of the groups $R^2$ are groups containing from 30 to 42 carbon atoms. The other groups $R^2$ are $C_4$ to $C_{19}$ and better still $C_4$ to $C_{12}$ hydrogen-containing groups. Preferably, $R^3$ represents a $C_2$ to $C_{36}$ hydrocarbon-based group or a polyoxyalkylene group and $R^4$ represents a hydrogen atom. Preferably, $R^3$ represents a $C_2$ to $C_{12}$ hydrocarbon-based group.

The hydrocarbon-based groups may be linear, cyclic or branched, and saturated or unsaturated groups. Moreover, the alkyl and alkylene groups may be linear or branched, and saturated or unsaturated groups.

In general, the polymers of formula (I) are in the form of mixtures of polymers, these mixtures also possibly containing a synthetic product corresponding to a compound of formula (I) in which n is 0, i.e. a diester.

As examples of polymers comprising at least two groups capable of interacting via hydrogen bonding, which may be used in the compositions according to the invention, mention may be made of the commercial products sold by the company Arizona Chemical under the names Uniclear 80 and Uniclear 100. They are sold, respectively, in the form of an 80% (in terms of active material) gel in a mineral oil and a 100% (in terms of active material) gel. They have a softening point of from 88 to 94° C. These commercial products are a mixture of copolymers of a C36 diacid condensed with ethylenediamine, having a weight-average molecular mass of about 6000. The terminal ester groups result from the esterification of the remaining acid endings with cetyl alcohol, stearyl alcohol or mixtures thereof (also known as cetylstearyl alcohol).

As polymers comprising at least two groups capable of interacting via hydrogen bonding, which may be used in the compositions according to the invention, mention may also be made of polyamide resins resulting from the condensation of an aliphatic dicarboxylic acid and a diamine (including compounds containing more than 2 carbonyl groups and 2 amine groups), the carbonyl and amine groups of adjacent individual units being condensed via an amide bond. These polyamide resins are, in particular, those sold under the brand name Versamid® by the companies General Mills Inc. and Henkel Corp. (Versamid 930, 744 or 1655) or by the company Olin Mathieson Chemical Corp. under the brand name Onamid®, in particular Onamid S or C. These resins have a weight-average molecular mass ranging from 6000 to 9000. For further information regarding these polyamides, reference may be made to the documents U.S. Pat. No. 3,645,705 and U.S. Pat. No. 3,148,125. More especially, Versamid® 930 or 744 is used.

The polyamides sold by the company Arizona Chemical under the references Uni-Rez (2658, 2931, 2970, 2621, 2613, 2624, 2665, 1554, 2623 and 2662) and the product sold under the reference Macromelt 6212 by the company Henkel may also be used. For further information regarding these polyamides, reference may be made to document U.S. Pat. No. 5,500,209.

It is also possible to use polyamide resins, such as those disclosed in U.S. Pat. No. 5,783,657 and U.S. Pat. No. 5,998,570.

The polymer present in the composition according to the invention advantageously has a softening point of greater than 65° C., which may be up to 190° C. It preferably has a softening point ranging from 70° C. to 130° C. and better still from 80° C. to 105° C.

The compositions may also comprise at least one additional polymer.
Additional Polymer The compositions according to the invention may contain a film-forming or non-film-forming additional polymer.

In the present invention, the term "film-forming polymer" means a polymer that is capable, by itself or in the presence of an auxiliary film-forming agent, of forming a macroscopically continuous deposit on keratin materials. The composition may comprise an aqueous phase and the additional polymer may be present in this aqueous phase. In this case, the polymer will preferably be a polymer in dispersion or an amphiphilic or associative polymer.

The term "polymer in dispersion" means water-insoluble polymers present in the form of particles of variable size. The polymer may or may not be crosslinked. The size of the polymer particles is typically between 25 and 500 nm and preferably between 50 and 200 nm. The following polymers in aqueous dispersion may be used: Ultrasol 2075 from Ganz Chemical, Daitosol 5000 AD from Daito Kasei, Avalure UR 450 from Noveon, Dynamx from National Starch, Syntran 5760 from Interpolymer, Acusol OP 301 and from Rohm & Haas, and Neocryl A 1090 from Avecia.

The acrylic dispersions sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® by the company Dow Chemical, Daitosol 5000 AD® or Daitosol 5000 SJ® by the company Daito Kasey Kogyo; Syntran 5760® by the company Interpolymer, Soltex OPT by the company Rohm & Haas, aqueous dispersions of acrylic or styrene/acrylic polymers sold under the brand name Joncryl® by the company Johnson Polymer, or the aqueous dispersions of polyurethane sold under the names Neorez R-981® and Neorez R-974® by the company Avecia-Neoresins, Avalure UR-405®, Avalure UR-410®, Avalure UR-425®, Avalure UR-450®, Sancure 875®, Sancure 861®, Sancure 878® and Sancure 2060® by the company Goodrich, Impranil 85® by the company Bayer and Aquamere H-1511® by the company Hydromer; the sulfopolyesters sold under the brand name Eastman AQ® by the company Eastman Chemical Products, and vinyl dispersions, for instance Mexomer PAM® from the company Chimex, and mixtures thereof, are other examples of aqueous dispersions of water-dispersible film-forming polymer particles.

The term "amphiphilic or associative polymers" means polymers comprising one or more hydrophilic parts that make them partially water-soluble and one or more hydrophobic parts via which the polymers associate or interact. The following associative polymers may be used: Nuvis FX 1100 from Elementis, Aculyn 22, Aculyn 44 and Aculyn 46 from Rohm & Haas, Viscophobe DB 1000 from Amerchol. Diblock copolymers formed from a hydrophilic block (polyacrylate or polyethylene glycol) and from a hydrophobic block (polystyrene or polysiloxane) may also be used.

The composition may comprise an oily phase and the film-forming polymer may be present in this oily phase. The polymer may then be in dispersion or in solution.

As examples of lipodispersible nonaqueous film-forming polymer dispersions in the form of nonaqueous dispersions of polymer particles in one or more silicone and/or hydrocarbon-based oils, which may be surface-stabilized with at least one stabilizer, especially a block, grafted or random polymer, mention may be made of acrylic dispersions in isododecane, for instance Mexomer PAP® from the company Chimex, and dispersions of particles of a grafted ethylenic polymer, preferably an acrylic polymer, in a liquid fatty phase, the ethylenic polymer advantageously being dispersed in the absence of additional stabilizer at the surface of the particles as described especially in document WO 04/055 081.

Among the additional film-forming polymers that may be used in the composition of the present invention, mention may be made of synthetic polymers, of free-radical type or of polycondensate type, and polymers of natural origin, and mixtures thereof.

The expression "free-radical film-forming polymer" means a polymer obtained by polymerization of unsaturated and especially ethylenically unsaturated monomers, each monomer being capable of homopoly-merizing (unlike polycondensates).

The film-forming polymers of free-radical type may be, in particular, vinyl polymers or copolymers, in particular acrylic polymers.

The vinyl film-forming polymers may result from the polymerization of ethylenically unsaturated monomers containing at least one acidic group and/or esters of these acidic monomers and/or amides of these acidic monomers.

Monomers bearing an acidic group that may be used are α,β-ethylenic unsaturated carboxylic acids such as acrylic acid, methacrylic acid, crotonic acid, maleic acid or itaconic acid. (Meth)acrylic acid and crotonic acid are preferably used, and more preferably (meth)acrylic acid.

The esters of acidic monomers are advantageously chosen from (meth)acrylic acid esters (also known as (meth)acrylates), especially (meth)acrylates of an alkyl, in particular of a $C_1$-$C_{30}$ and preferably $C_1$-$C_{20}$ alkyl, (meth)acrylates of an aryl, in particular of a $C_6$-$C_{10}$ aryl, and (meth)acrylates of a hydroxyalkyl, in particular of a $C_2$-$C_6$ hydroxyalkyl.

The film-forming polymer may be chosen from block or random polymers and/or copolymers especially comprising polyurethanes, polyacrylics, silicones, fluoro polymers, butyl rubbers, ethylene copolymers, natural gums and polyvinyl alcohols, and mixtures thereof.

The vinyl film-forming polymers may also result from the homopolymerization or copolymerization of monomers chosen from vinyl esters and styrene monomers.

Examples of vinyl esters that may be mentioned are vinyl acetate, vinyl neodecanoate, vinyl pivalate, vinyl benzoate and vinyl t-butylbenzoate.

Styrene monomers that may be mentioned are styrene and α-methylstyrene.

Among the film-forming polycondensates that may be mentioned are polyurethanes, polyesters, polyester-amides, polyamides, epoxyester resins and polyureas.

The polyurethanes may be chosen from anionic, cationic, nonionic and amphoteric polyurethanes, polyurethane-acrylics, polyurethane-polyvinylpyrrolidones, poly-ester-polyurethanes, polyether-polyurethanes, polyureas and polyurea-polyurethanes, and mixtures thereof.

The polyesters may be obtained, in a known manner, by polycondensation of dicarboxylic acids with polyols, in particular dials.

According to one example of a composition according to the invention, the film-forming polymer may be a polymer dissolved in a liquid fatty phase comprising organic solvents or oils (the film-forming polymer is thus said to be a liposoluble polymer). The liquid fatty phase preferably comprises a volatile oil, optionally mixed with a nonvolatile oil.

Examples of liposoluble polymers that may be mentioned are copolymers of vinyl ester (the vinyl group being directly linked to the oxygen atom of the ester group and the vinyl ester containing a saturated, linear or branched hydrocarbon-based radical of 1 to 19 carbon atoms, linked to the carbonyl of the ester group) and of at least one other monomer which may be a vinyl ester (other than the vinyl ester already present), an α-olefin (containing from 8 to 28 carbon atoms), an alkyl vinyl ether (in which the alkyl group comprises from 2 to 18 carbon atoms) or an allylic or methallylic ester (containing a saturated, linear or branched hydrocarbon-based radical of 1 to 19 carbon atoms, linked to the carbonyl of the ester group).

These copolymers may be crosslinked with the aid of crosslinking agents, which may be either of the vinyl type or of the allylic or methallylic type, such as tetraallyloxyethane, divinylbenzene, divinyl octane-dioate, divinyl dodecanedio-ate and divinyl octadecane-dioate.

Examples of liposoluble film-forming polymers that may be mentioned include copolymers of a vinyl ester and of at least one other monomer that may be a vinyl ester, especially vinyl neodecanoate, vinyl benzoate and vinyl t-butylbenzoate, an α-olefin, an alkyl vinyl ether or an allylic or methallylic ester.

Examples of liposoluble film-forming polymers that may also be mentioned are liposoluble copolymers, and in particular those resulting from the copolymerization of vinyl esters containing from 9 to 22 carbon atoms or of alkyl acrylates or methacrylates, and alkyl radicals containing from 10 to 20 carbon atoms.

Such liposoluble copolymers may be chosen from copolymers of polyvinyl stearate, polyvinyl stearate crosslinked with the aid of divinylbenzene, of diallyl ether or of diallyl phthalate, polystearyl (meth)acrylate, polyvinyl laurate and polylauryl (meth)acrylate, it being possible for these poly (meth)acrylates to be crosslinked with the aid of ethylene glycol dimethacrylate or tetraethylene glycol dimethacrylate.

The liposoluble copolymers defined above are known and are described in particular in patent application FR-A-2 232 303; they may have a weight-average molecular weight ranging from 2000 to 500 000 and preferably from 4000 to 200 000.

As liposoluble film-forming polymers that may be used in the invention, mention may also be made of polyalkylenes and in particular copolymers of C2-C20 alkenes, such as polybutene, alkylcelluloses with a linear or branched, saturated or unsaturated C1-C8 alkyl radical, for instance ethylcellulose and propylcellulose.

The composition according to the invention may comprise a plasticizer that promotes the formation of a film with the film-forming polymer. Such a plasticizer may be chosen from any compound known to those skilled in the art as being capable of fulfilling the desired function.

Semi Crystalline Polymer

The composition according to the invention may also advantageously comprise at least one semicrystalline polymer of organic structure whose melting point is greater than or equal to 30° C.

Preferably, the total amount of semicrystalline polymer(s) represents from 0.1% to 45% of the total weight of the composition, better still from 0.5% to 40%, for example from 1% to 35% by weight, better still from 1% to 20%, or from 3% to 30%, 5% to 30% or even 15% to 30%. It preferably represents from 2% to 10% by weight of the composition.

For the purposes of the invention, the term "polymers" means compounds containing at least two repeating units, preferably at least three repeating units and more especially at least ten repeating units.

For the purposes of the invention, the term "semicrystalline polymer" means polymers comprising a crystallizable portion and an amorphous portion in the backbone and having a first-order reversible change of phase temperature, in particular of melting (solid-liquid transition). The crystallizable portion is either a side chain (or pendent chain) or a block in the backbone.

When the crystallizable portion of the semicrystalline polymer is a block of the polymer backbone, this crystallizable block has a different chemical nature from that of the amorphous blocks; in this case, the semicrystalline polymer is a block copolymer, for example of the diblock, triblock or multiblock type. When the crystallizable portion is a chain that is pendent on the backbone, the semicrystalline polymer may be a homopolymer or a copolymer.

The terms "organic compound" and "having an organic structure" mean compounds containing carbon atoms and hydrogen atoms and optionally heteroatoms such as S, O, N or P, alone or in combination.

The melting point of the semicrystalline polymer is preferably less than 150° C.

The melting point of the semicrystalline polymer is preferably greater than or equal to 30° C. and less than 100° C. More preferably, the melting point of the semicrystalline polymer is preferably greater than or equal to 30° C. and less than 70° C.

The semicrystalline polymer(s) according to the invention are solid at room temperature (25° C.) and atmospheric pressure (760 mmHg), with a melting point of greater than or equal to 30° C. The melting point values correspond to the melting point measured using a differential scanning calorimeter (DSC), such as the calorimeter sold under the name DSC 30 by the company Mettler, with a temperature rise of 5 or 10° C. per minute (the melting point under consideration is the point corresponding to the temperature of the most endothermic peak of the thermogram).

The semicrystalline polymer(s) according to the invention preferably have a melting point that is higher than the temperature of the keratinous support intended to receive said composition, in particular the skin or the lips.

According to the invention, the semicrystalline polymers are advantageously soluble in the fatty phase, especially to at least 1% by weight, at a temperature that is higher than their melting point. Besides the crystallizable chains or blocks, the blocks of the polymers are amorphous.

For the purposes of the invention, the expression "crystallizable chain or block" means a chain or block which, if it were obtained alone, would change from the amorphous state to the crystalline state reversibly, depending on whether one is above or below the melting point. For the purposes of the invention, a "chain" is a group of atoms, which are pendent or lateral relative to the polymer backbone. A "block" is a group of atoms belonging to the backbone, this group constituting one of the repeating units of the polymer.

Preferably, the polymer backbone of the semicrystalline polymers is soluble in the fatty phase at a temperature above their melting point.

Preferably, the crystallizable blocks or chains of the semicrystalline polymers represent at least 30% of the total weight of each polymer and better still at least 40%. The semicrystalline polymers containing crystallizable side chains are homopolymers or copolymers. The semicrystalline polymers of the invention containing crystallizable blocks are block or multiblock copolymers. They may be obtained by polymerizing a monomer containing reactive for ethylenic) double bonds or by polycondensation. When the polymers of the invention are polymers containing crystallizable side chains, these side chains are advantageously in random or statistical form.

Preferably, the semicrystalline polymers of the invention are of synthetic origin.

According to one preferred embodiment, the semicrystalline polymer is chosen from:
homopolymers and copolymers comprising units resulting from the polymerization of one or more monomers bearing crystallizable hydrophobic side chains,
polymers bearing in the backbone at least one crystallizable block,
polycondensates of aliphatic or aromatic or aliphatic/aromatic polyester type,
copolymers of ethylene and propylene prepared via metallocene catalysis.

The semicrystalline polymers that may be used in the invention may be chosen in particular from:
block copolymers of polyolefins of controlled crystallization, whose monomers are described in EP-A-0 951 897,
polycondensates, especially of aliphatic or aromatic polyester type or of aliphatic/aromatic polyester type,
copolymers of ethylene and propylene prepared via metallocene catalysis,
homopolymers or copolymers bearing at least one crystallizable side chain and homopolymers or copolymers bearing at least one crystallizable block in the backbone, for instance those described in document U.S. Pat. No. 5,156,911,
homopolymers or copolymers bearing at least one crystallizable side chain, in particular bearing fluoro group(s), such as those described in document WO-A-01/19333, and mixtures thereof.

In the last two cases, the crystallizable side chain(s) or block(s) is (are) hydrophobic.

A) Semicrystalline Polymers Containing Crystallizable Side Chains

Mention may be made in particular of those defined in documents U.S. Pat. No. 5,156,911 and WO-A-01/19333.

They are homopolymers or copolymers comprising from 50% to 100% by weight of units resulting from the polymerization of one or more monomers bearing a crystallizable hydrophobic side chain.

These homopolymers or copolymers are of any nature, provided that they meet the conditions mentioned hereinbelow with, in particular, the characteristic of being soluble or dispersible in the fatty phase, by heating above their melting point mp. They can result:
from the polymerization, especially the free-radical polymerization, of one or more monomers containing reactive or ethylenic double bond(s) with respect to a polymerization, namely a vinyl, (meth)acrylic or allylic group,
from the polycondensation of one or more monomers bearing co-reactive groups (carboxylic acid, sulfonic acid, alcohol, amine or isocyanate), for instance polyesters, polyurethanes, polyethers or polyureas.

a) In general, the crystallizable units (chains or blocks) of the semicrystalline polymers according to the invention are derived from monomer(s) containing crystallizable block(s) or chain(s), used for manufacturing semicrystalline polymers. These polymers are chosen especially from homopolymers and copolymers resulting from the polymerization of at least one monomer containing crystallizable chain(s) that may be represented by formula X:

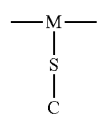

with M representing an atom of the polymer backbone,
C representing a crystallizable group, and
S representing a spacer.

The crystallizable chains "—S—C" may be aliphatic or aromatic, and optionally fluorinated or perfluorinated. "C" especially represents a group $(CH_2)_n$, which may be linear or branched or cyclic, with n being an integer ranging from 12 to 40. Preferably, "C" is a linear group. Preferably, "S" and "C" are different.

When the crystallizable chains are hydrocarbon-based aliphatic chains, they comprise hydrocarbon-based alkyl chains containing at least 12 carbon atoms and not more than 40 carbon atoms and better still not more than 24 carbon atoms. They are especially aliphatic chains or alkyl chains containing at least 12 carbon atoms, and they are preferably $C_{14}$-$C_{24}$, preferably $C_{16}$-$C_{22}$ alkyl chains. When they are fluoroalkyl or perfluoroalkyl chains, they contain at least 11 carbon atoms, at least 6 of which carbon atoms are fluorinated.

As examples of semicrystalline homopolymers or copolymers containing crystallizable chain(s), mention may be made of those resulting from the polymerization of one or more of the following monomers: (meth)acrylates of saturated alkyls with the alkyl group being $C_{14}$-$C_{24}$, perfluoroalkyl (meth)acrylates with a $C_{11}$-$C_{15}$ perfluoroalkyl group, N-alkyl(meth)acrylamides with the alkyl group being $C_{14}$ to $C_{24}$ with or without a fluorine atom, vinyl esters containing alkyl or perfluoroalkyl chains with the alkyl group being $C_{14}$ to $C_{24}$ (with at least 6 fluorine atoms per perfluoroalkyl chain), vinyl ethers containing alkyl or perfluoroalkyl chains with the alkyl group being $C_{14}$ to $C_{24}$ and at least 6 fluorine atoms per perfluoroalkyl chain, $C_{14}$ to $C_{24}$ α-olefins such as, for example, octadecene, para-alkylstyrenes with an alkyl group containing from 12 to 24 carbon atoms, and mixtures thereof.

When the polymers result from a polycondensation, the hydrocarbon-based and/or fluorinated crystallizable chains as defined above are borne by a monomer that may be a diacid, a diol, a diamine or a diisocyanate.

When the polymers that are the subject of the invention are copolymers, they additionally contain from 0 to 50% of groups Y which is a polar or non-polar monomer or a mixture of the two.

When Y is a polar monomer, it is either a monomer bearing polyoxyalkylenated groups (especially oxyethylenated and/or oxypropylenated groups), a hydroxyalkyl (meth)acrylate, for instance hydroxyethyl acrylate, (meth) acrylamide, an N-alkyl(meth)acrylamide, an N,N-dialkyl(meth)acrylamide such as, for example, N,N-diisopropylacrylamide or N-vinylpyrrolidone (NVP), N-vinylcaprolactam, a monomer bearing at least one carboxylic acid group, for instance (meth) acrylic acid, crotonic acid, itaconic acid, maleic acid or fumaric acid, or bearing a carboxylic acid anhydride group, for instance maleic anhydride, and mixtures thereof.

When Y is a nonpolar monomer, it may be an ester of the linear, branched or cyclic alkyl (meth)acrylate type, a vinyl ester, an alkyl vinyl ether, an α-olefin, styrene or styrene substituted with a $C_1$ to $C_{10}$ alkyl group, for instance α-methylstyrene, or a macromonomer of the polyorganosiloxane type containing vinyl unsaturation.

For the purposes of the invention, the term "alkyl" means a saturated group especially of $C_8$ to $C_{24}$, except where otherwise mentioned.

Preferably, the semicrystalline polymers containing a crystallizable side chain are alkyl (meth)acrylate or alkyl(meth) acrylamide homopolymers with an alkyl group as defined above, and especially of $C_{14}$-$C_{24}$, copolymers of these monomers with a hydrophilic monomer preferably of different nature from (meth)acrylic acid, for instance N-vinylpyrrolidone or hydroxyethyl (meth)acrylate, and mixtures thereof.

Advantageously, the semicrystalline polymer(s) containing a crystallizable side chain has (have) a weight-average molecular mass Mp ranging from 5000 to 1 000 000, preferably from 10 000 to 800 000, preferentially from 15 000 to 500 000 and more preferably from 100 000 to 200 000.

As a particular example of a semicrystalline polymer that may be used in the composition according to the invention, mention may be made of the Intelimer® products from the company Landec described in the brochure "Intelimer® polymers", Landec IP22 (Rev. 4-97), These polymers are in solid form at room temperature (25° C.). They bear crystallizable side chains and have the preceding formula X. They are poly($C_{10}$-$C_{30}$)alkyl acrylates, which are particularly suitable as semicrystalline polymers that may be included in a composition in accordance with the present invention. These polymers may especially have a molecular weight ranging from 15 000 to 500 000 and preferably from 100 000 to 200 000.

For example, the product Intelimer® IPA 13-1 from the company Landec is chosen, which is a polystearyl acrylate with a molecular weight of about 145 000 and a melting point of 49° C.

The semicrystalline polymers may especially be those described in Examples 3, 4, 5, 7 and 9 of patent U.S. Pat. No. 5,156,911, and more particularly from the copolymerization:
  of acrylic acid, of hexadecyl acrylate and of isodecyl acrylate in a 1/16/3 ratio,
  of acrylic acid and of pentadecyl acrylate in a 1/19 ratio,
  of acrylic acid, of hexadecyl acrylate and of ethyl acrylate in a 2.5/76.5/20 ratio,
  of acrylic acid, of hexadecyl acrylate and of methyl acrylate in a 5/85/10 ratio,
  of acrylic acid and of polyoctadecyl (meth)acrylate in a 2.5/97.5 ratio.

It is also possible to use the polymer Structure "O" from National Starch, such as the product described in document U.S. Pat. No. 5,736,125 with a melting point of 44° C.

The semicrystalline polymers may in particular be semicrystalline polymers with crystallizable pendent chains comprising fluoro groups, as described in Examples 1, 4, 6, 7 and 8 of document WO-A-01/19333.

It is also possible to use the semicrystalline polymers obtained by copolymerization of stearyl acrylate and of acrylic acid or of NVP, as described in document U.S. Pat. No. 5,519,063 or EP-A-550 745.

It is also possible to use the semicrystalline polymers obtained by copolymerization of behenyl acrylate and of acrylic acid or of NVP, as described in documents U.S. Pat. No. 5,519,063 and EP-A-550 745 and more especially those described in Examples 3 and 4 below, of polymer preparation.

B) Polymers Bearing at Least One Crystallizable Block in the Backbone

This is also a case of polymers that are soluble or dispersible in the fatty phase by heating above their melting point rap. These polymers are especially block copolymers consisting of at least two blocks of different chemical nature, one of which is crystallizable.

The polymer bearing at least one crystallizable block in the backbone may be chosen from block copolymers of olefin or of cycloolefin containing a crystallizable chain, for instance those derived from the block polymerization of:
  cyclobutene, cyclohexene, cyclooctene, norbornene (i.e. bicyclo(2,2,1)-2-heptene), 5-methylnorbornene, 5-ethylnorbornene, 5,6-dimethylnorbornene, 5,5,6-trimethylnorbornene, 5-ethylidenenorbornene, 5-phenylnorbornene, 5-benzylnorbornene, 5-vinylnor-bornene, 1,4,5,8-dimethano-1,2,3,4,4a,5,8a-octahydronaphthalene, dicyclopentadiene, or mixtures thereof, with ethylene, propylene, 1-butene, 3-methyl-1-butene, 1-hexene, 4-methyl-1-pentene, 1-octene, 1-decease or 1-eicosene, or mixtures thereof,
and in particular copoly(ethylene/norbornene) blocks and (ethylene/propylene/ethylidene-norbornene) block terpolymers. Those resulting from the block copolymerization of at least two $C_2$-$C_{16}$, better still $C_2$-$C_{12}$ α-olefins such as those mentioned above and in particular block bipolymers of ethylene and of 1-octene may also be used.

The polymer bearing at least one crystallizable block in the backbone may be chosen from copolymers containing at least one crystallizable block, the rest of the copolymer being amorphous (at room temperature). These copolymers may also contain two crystallizable blocks of different chemical nature.

The preferred copolymers are those that simultaneously contain at room temperature a crystallizable block and an amorphous block that are both hydrophobic and lipophilic, sequentially distributed; mention may be made, for example, of polymers containing one of the crystallizable blocks and one of the amorphous blocks below:

Block that is crystallizable by nature, of polyester type, for instance poly(alkylene terephthalate), or of polyolefin type, for instance polyethylenes or polypropylenes.

Amorphous and lipophilic block, for instance: amorphous polyolefins or copoly(olefin)s such as poly(isobutylene), hydrogenated polybutadiene or hydrogenated poly(isoprene).

As examples of such copolymers containing a crystallizable block and an amorphous block, mention may be made of:
α) poly(ϵ-caprolactone)-b-poly(butadiene) block copolymers, preferably used hydrogenated, such as those described in the article D6 "Melting behavior of poly(-caprolactone)-block-polybutadiene copolymers" from S, Nojima, Macromolecules, 32, 3727-3734 (1999),
β) the hydrogenated block or multiblock polybutylene terephthalate)-b-poly(isoprene) block copolymers cited in the article D7 "Study of morphological and mechanical properties of PP/PBT" by B. Boutevin et al., Polymer Bulletin, 34, 117-123 (1995),
γ) the poly(ethylene)-b-copoly(ethylene/propylene) block copolymers cited in the articles D8 "Morphology of semicrystalline block copolymers of ethylene-(ethylene-alt-propylene)" by P. Rangarajan et al., Macromolecules, 26, 4640-4645 (1993) and D9 "Polymer aggregates with crystalline cores: the system poly(ethylene)-poly(ethylene-propylene)" by P. Richter et al., Macromolecules, 30, 1053-1068 (1997),
δ) the poly(ethylene)-b-poly(ethylethylene) block copolymers cited in the general article D10 "Crystallization in block copolymers" by I. W. Hamley, Advances in Polymer Science, Vol. 148, 113-137 (1999).

C) Polycondensates of Aliphatic or Aromatic or Aliphatic/Aromatic Polyester Type The polyester polycondensates may be chosen from aliphatic polyesters. Their molar mass is preferably greater than or equal to 200 and less than or equal to 10 000, and more preferably greater than or equal to 300 and less than or equal to 5000, preferably greater than or equal to 500 and greater than or equal to 2000 g/mol.

The polyester polycondensates are in particular chosen from polycaprolactones. In particular, the polycaprolactones may be chosen from ϵ-caprolactone homopolymers. The homopolymerization may be initiated with a diol, especially a diol containing from 2 to 10 atoms, such as diethylene glycol, 1,4-butanediol or neopentyl glycol.

Polycaprolactones may be used for example, especially those sold under the name CAPA® 240 (melting point of 68° C. and molecular weight of 4000), 223 (melting point of 48° C. and molecular weight of 2000), 222 (melting point of 48° C. and molecular weight of 2000), 217 (melting point of 44° C. and molecular weight of 1250), 2125 (melting point of 45° C. and molecular weight of 1250), 212 (melting point of 45° C. and molecular weight of 1000), 210 (melting point of 38° C. and molecular weight of 1000), 205 (melting point of 39° C. and molecular weight of 830) by the company Solvay, or PCL-300 and PCL-700 by the company Union Carbide.

CAPA® 2125 whose melting point is between 35 and 45° C. and whose molecular weight is equal to 1250 may be used in particular.

The semicrystalline polymers in the composition of the invention may or may not be partially crosslinked, provided that the degree of crosslinking does not interfere with their dissolution or dispersion in the fatty phase by heating above their melting point. It may then be a chemical crosslinking, by reaction with a multifunctional monomer during the polymerization. It may also be a physical crosslinking which may, in this case, be due either to the establishment of bonds of hydrogen or dipolar type between groups borne by the polymer, such as, for example, the dipolar interactions between carboxylate ionomers, these interactions being of small amount and borne by the polymer backbone; or to a phase separation between the crystallizable blocks and the amorphous blocks borne by the polymer.

Preferably, the semicrystalline polymers in the composition according to the invention are noncrosslinked.

D) Copolymers of Ethylene and Propylene Prepared Via Metallocene Catalysis

The semicrystalline polymer of the composition of the invention may also be a polymer obtained via metallocene catalysis, such as those described in patent US 2007/0 031 361, the content of which is incorporated herein by reference.

These polymers are copolymers of ethylene and propylene prepared via metallocene catalysis, i.e. by polymerization at low pressure and in the presence of a metallocene catalyst.

The weight-average molecular mass (Mw) of these polymers obtained via metallocene catalysis described in this document is less than or equal to 25 000 g/mol and ranges, for example, from 2000 to 22 000 g/mol and better still from 4000 to 20 000 g/mol.

The number-average molecular mass (Mn) of these copolymers obtained via metallocene catalysis described in this document is preferably less than or equal to 15 000 g/mol and ranges, for example, from 1000 to 12 000 g/mol and better still from 2000 to 10 000 g/mol.

The polydispersity index I of the polymer is equal to the ratio of the weight-average molecular mass Mw to the number-average molecular mass Mn.

Preferably, the polydispersity index of the copolymers is between 1.5 and 10, preferably between 1.5 and 5, preferably between 1.5 and 3 and better still between 2 and 2.5.

The copolymers may be obtained in a known manner from ethylene and/or propylene monomers, for example via metallocene catalysis according to the process described in document EP 571 882, the content of which is incorporated herein by reference.

The copolymers of ethylene and propylene prepared via metallocene catalysis may be unmodified or "polar"-modified (i.e. modified such that they contain polar groups). The polar-modified copolymers may be prepared in a known manner from unmodified homopolymers and copolymers such as those described previously by oxidation with gases containing oxygen, such as air, or by grafting with polar monomers such as maleic acid or acrylic acid or alternatively derivatives of these acids. These two routes enabling polar modification of the polyolefins obtained via metallocene catalysis are described, respectively, in documents EP 890 583 and U.S. Pat. No. 5,998,547, for example, the content of these two documents being incorporated herein by reference.

According to the present invention, the polar-modified copolymers of ethylene and/or propylene prepared via metallocene catalysis that are particularly preferred are polymers modified such that they have hydrophilic properties. Examples that may be mentioned include ethylene and/or propylene homopolymers or copolymers modified by the presence of hydrophilic groups such as maleic anhydride, acrylate, methacrylate, polyvinylpyrrolidone (PVP), etc.

Ethylene and/or propylene homopolymers or copolymers modified by the presence of hydrophilic groups such as maleic anhydride or acrylate are particularly preferred.

Examples that may be mentioned include:

polypropylene polymers modified with maleic anhydride (PPMA) sold by the company Clariant, or polypropylene-ethylene-maleic anhydride copolymers, such as those sold by the company Clariant under the name LicoCare, for instance LicoCare PP207 LP3349, LicoCare CM401 LP3345, LicoCare CA301 LP3346 and LicoCare CA302 LP3347.

In the context of a composition for the lips, a polar-modified polymer with a low degree of crystallinity, preferably of less than 40%, will be preferred.

Silicone Resin

The compositions in accordance with the invention may also comprise a silicone resin.

More generally, the term "resin" means a compound of three-dimensional structure. "Silicone resins" are also referred to as "siloxane resins". Thus, for the purposes of the present invention, a polydimethylsiloxane is not a silicone resin.

The nomenclature of silicone resins (also known as siloxane resins) is known under the name "MDTQ", the resin being described as a function of the various siloxane monomer units it comprises, each of the letters M, D, T and Q characterizing a type of unit.

The letter M represents the monofunctional unit of formula R1R2R3SiO$_{1/2}$, the silicon atom being bonded to only one oxygen atom in the polymer comprising this unit.

The letter D means a difunctional unit R1R2SiO$_{2/2}$ in which the silicon atom is bonded to two oxygen atoms.

The letter T represents a trifunctional unit of formula R1SiO$_{3/2}$.

Such resins are described, for example, in the *Encyclopaedia of Polymer Science and Engineering*, vol. 15, John Wiley & Sons, New York (1989), pp. 265-270 and U.S. Pat. No. 2,676,182, U.S. Pat. No. 3,627,851, U.S. Pat. No. 3,772,247, U.S. Pat. No. 5,248,739 or U.S. Pat. No. 5,082,706, U.S. Pat. No. 5,319,040, U.S. Pat. No. 5,302,685 and U.S. Pat. No. 4,935,484.

In the units M, D and T defined previously, R, i.e. R1, R2 and R3, represents a hydrocarbon-based radical (especially alkyl) containing from 1 to 10 carbon atoms, a phenyl group, a phenylalkyl group or a hydroxyl group.

Finally, the letter Q means a tetrafunctional unit SiO$_{4/2}$ in which the silicon atom is bonded to four hydrogen atoms, which are themselves bonded to the rest of the polymer.

Various silicone resins with different properties may be obtained from these various units, the properties of these polymers varying as a function of the type of monomer (or unit), of the nature and number of the radical R, of the length of the polymer chain, of the degree of branching and of the size of the side chains.

As silicone resins that may be used in the compositions according to the invention, silicone resins of MQ type, of T type or of MQT type may be used, for example.

MQ Resins:

As examples of silicone resins of MQ type, mention may be made of the alkyl siloxysilicates of formula [(R1)$_3$SiO$_{1/2}$]$_x$(SiO$_{4/2}$)$_y$ (MQ units) in which x and y are integers ranging from 50 to 80, and such that the group R1 represents a radical as defined previously, and is preferably an alkyl group containing from 1 to 8 carbon atoms or a hydroxyl group, preferably a methyl group.

As examples of solid silicone resins of MQ type of the trimethyl siloxysilicate type, mention may be made of those sold under the reference SR1000 by the company General Electric, under the reference TMS 803 by the company Wacker, under the name KF-7312J by the company Shin-Etsu, or DC749 and DC593 by the company Dow Corning.

As silicone resins comprising siloxysilicate MQ units, mention may also be made of phenylalkyl siloxysilicate resins, such as phenylpropyl dimethylsiloxysilicate (Silshine 151 sold by the company General Electric). The preparation of such resins is especially described in U.S. Pat. No. 5,817,302.

T Resins:

As examples of silicone resins of T type, mention may be made of polysilsesquioxanes of formula (RSiO$_{3/2}$)$_x$ (T units) in which x is greater than 100 and such that the group R is an alkyl group containing from 1 to 10 carbon atoms, said polysilsesquioxanes also possibly comprising Si—OH end groups.

Use may preferably be made of polymethylsilsesquioxane resins in which R represents a methyl group, for instance those sold:

by the company Wacker under the reference Resin MK such as Belsil PMS MK: polymer comprising CH$_3$SiO$_{3/2}$ repeating units (T units), which may also comprise up to 1% by weight of (CH$_3$)$_2$SiO$_{2/2}$ units (D units) and with an average molecular weight of about 10 000 g/mol, or by the company Shin-Etsu under the reference KR-220L, which are compounds of T units of formula CH$_3$SiO$_{3/2}$ and contain Si—OH (silanol) end groups, under the reference KR-242A, which comprise 98% of T units and 2% of dimethyl D units and contain Si—OH end groups, or under the reference KR-251 comprising 88% of T units and 12% of dimethyl D units and containing Si—OH end groups.

MQT Resins:

Resins comprising MQT units that are especially known are those mentioned in document U.S. Pat. No. 5,110,890.

A preferred form of resins of MQT type are MQT-propyl resins (also known as MQTPr). Such resins that may be used in the compositions according to the invention are especially those described and prepared in patent application WO 2005/075 542, the content of which is incorporated herein by reference.

The MQ-T-propyl resin preferably comprises the following units:

(i) (R$^1$$_3$SiO$_{1/2}$)$_a$
(ii) (R$^2$$_2$SiO$_{2/2}$)$_b$
(iii) (R$^3$SiO$_{3/2}$)$_c$ and
(iv) (SiO$_{4/2}$)$_d$ with R$^1$, R$^2$ and R$^3$ independently representing a hydrocarbon-based radical (especially alkyl) containing from 1 to 10 carbon atoms, a phenyl group, a phenylalkyl group or a hydroxyl group, and preferably an alkyl radical containing from 1 to 8 carbon atoms or a phenyl group, a, b, c and d being mole fractions,
a being between 0.05 and 0.5,
b being between 0 and 0.3,
c being greater than 0,
d being between 0.05 and 0.6, $$a+b+c+d=1,$$

on condition that more than 40 mol % of the groups R3 of the siloxane resin are propyl groups.

Preferably, the siloxane resin comprises the following units:
(i) $(R1_3SiO_{1/2})_a$
(iii) $(R3SiO_{3/2})_b$ and
(iv) $(SiO_{4/2})$
with
R1 and R3 independently representing an alkyl group containing from 1 to 8 carbon atoms, R1 preferably being a methyl group and R3 preferably being a propyl group,
a being between 0.05 and 0.5, preferably between 0.15 and 0.4,
c being greater than 0, preferably between 0.15 and 0.4,
d being between 0.05 and 0.6, preferably between 0.2 and 0.6, or between 0.2 and 0.55, $$a+b+c+d=1,$$

on condition that more than 40 mold of the groups R3 of the siloxane resin are propyl groups.

The siloxane resins that may be used according to the invention may be obtained via a process comprising the reaction of:
A) an MQ resin comprising at least 80 mol % of units $(R1_3SiO_{1/2})_a$ and $(SiO_{4/2})_d$,
R1 representing an alkyl group containing from 1 to 8 carbon atoms, an aryl group, a carbinol group or an amino group,
a and d being greater than 0,
the ratio a/d being between 0.5 and 1.5;
and
B) a T-propyl resin comprising at least 80 mol % of units $(R3SiO_{3/2})_c$,
R3 representing an alkyl group containing from 1 to 8 carbon atoms, an aryl group, a carbinol group or an amino group,
c being greater than 0,
on condition that at least 40 mol % of the groups R3 are propyl groups,
in which the mass ratio A/B is between 95/5 and 15/85, and the mass ratio A/B is preferably 30/70.

Advantageously, the mass ratio A/B is between 95/5 and 15/85. Preferably, the ratio A/B is less than or equal to 70/30. These preferred ratios have been found to afford comfortable deposits.

Preferably, when it is present, the siloxane resin is present in the composition in a total resin solids content ranging from 3% to 40% by weight, preferably ranging from 4% to 30% by weight and better still ranging from 4% to 25% by weight relative to the total weight of the composition.

Dyestuffs

The compositions according to the invention may advantageously contain a coloring agent, which may be chosen from water-soluble or liposoluble dyes, pigments and nacres, and mixtures thereof.

The composition according to the invention may also comprise one or more dyestuffs chosen from water-soluble dyes and pulverulent dyestuffs, for instance pigments, nacres and glitter flakes that are well known to those skilled in the art. The dyestuffs may be present in the composition in a content ranging from 0.01% to 50% by weight and preferably from 0.01% to 30% by weight, and in particular from 0.05% to 25% by weight, relative to the weight of the composition.

The term "pigments" should be understood as meaning white or colored, mineral or organic particles, which are insoluble in an aqueous solution and which are intended to color and/or opacify the resulting film.

The pigments may be present in a proportion of from 0.01% to 20% by weight, especially from 0.01% to 15% by weight and in particular from 0.02% to 10% by weight relative to the total weight of the cosmetic composition.

As mineral pigments that may be used in the invention, mention may be made of titanium oxide, zirconium oxide or cerium oxide, and also zinc oxide, iron oxide or chromium oxide, ferric blue, manganese violet, ultramarine blue and chromium hydrate.

They may also be pigments with a structure that may be, for example, of sericite/brown iron oxide/titanium dioxide/silica type. Such a pigment is sold, for example, under the reference Coverleaf NS or JS by the company Chemicals and Catalysts.

The dyestuff may also comprise a pigment with a structure that may be, for example, of silica microsphere type containing iron oxide. An example of a pigment having this structure is the product sold by the company Miyoshi under the reference PC Ball PC-LL-100 P, this pigment being formed from silica microspheres containing yellow iron oxide.

Among the organic pigments that may be used in the invention, mention may be made of carbon black, pigments of D&C type, lakes based on cochineal carmine or on barium, strontium, calcium or aluminum, or alternatively the diketopyrrolopyrroles (DPP) described in documents EP-A-542 669, EP-A-787 730, EP-A-787 731 and WO-A-96/08537.

The term "nacres" should be understood as meaning iridescent or non-iridescent colored particles of any form, especially produced by certain molluscs in their shell, or else synthesized, and which have a color effect by optical interference.

The nacres may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles at the surface of which are superposed at least two successive layers of metal oxides and/or of organic dyestuffs.

Examples of nacres that may also be mentioned include natural mica coated with titanium oxide, with iron oxide, with natural pigment or with bismuth oxychloride.

Among the nacres available on the market, mention may be made of the mica-based nacres Timica, Flamenco and Duochrome sold by the company Engelhard, the Timiron nacres sold by the company Merck, the Prestige mica-based nacres, sold by the company Eckart, and the Sunshine synthetic mica-based nacres, sold by the company Sun Chemical.

The nacres may more particularly have a yellow, pink, red, bronze, orangey, brown, gold and/or coppery color or tint.

As illustrations of nacres that may be used in the context of the present invention, mention may be made especially of the gold-colored nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona) and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Micronor); the brown nacres sold especially by the company Engelhard under the name Nu-antique copper 340XB (Cloisonne) and Brown CL4509 (Chromalite); the nacres with a copper tint sold especially by the company Engelhard under the name Copper 340A (Timica); the nacres with a red tint sold especially by the company Merck under the name Sienna fine (17386) (Colorona); the nacres with a yellow tint sold especially by the company Engelhard under the name Yellow (4502) (Chromalite); the red nacres with a gold tint sold especially by the company Engelhard under the name Sunstone G012 (Gemtone); the pink nacres sold especially by the company Engelhard under the name Tan opale G005 (Gemtone); the black nacres with a gold tint sold especially by the company Engelhard under the name Nu antique bronze 240 AB (Timica), the blue nacres sold especially by the company Merck under the name Matte blue (17433) (Microna), the white nacres with a silvery tint sold especially by the company Merck under the name Xirona Silver, and the golden-green pink-orange nacres sold especially by the company Merck under the name Indian summer (Xirona), and mixtures thereof.

The term "dyes" should be understood as meaning compounds that are generally organic, which are soluble in fatty substances such as oils or in an aqueous-alcoholic phase.

The liposoluble dyes may be chosen from Sudan red, DC Red 17, DC Green 6, β-carotene, Sudan brown, DC Yellow 11, DC Violet 2, DC Orange 5 and quinoline yellow. The water-soluble dyes are, for example, beetroot juice or methylene blue.

The cosmetic composition according to the invention may also contain at least one material with a specific optical effect.

This effect is different than a simple conventional hue effect, i.e. a unified and stabilized effect as produced by standard dyestuffs, for instance monochromatic pigments. For the purposes of the invention, the term "stabilized" means lacking an effect of variability of the color as a function of the angle of observation or alternatively in response to a temperature change.

For example, this material may be chosen from particles with a metallic tint, goniochromatic coloring agents, diffracting pigments, thermochromic agents, optical brighteners, and also fibers, especially interference fibers. Needless to say, these various materials may be combined so as to simultaneously afford two effects.

The particles with a metallic tint that may be used in the invention are chosen in particular from:
particles of at least one metal and/or of at least one metal derivative,
particles comprising a monomaterial or multimaterial organic or mineral substrate, at least partially coated with at least one coat with a metallic tint comprising at least one metal and/or at least one metal derivative, and mixtures of said particles.

Among the metals that may be present in said particles, mention may be made, for example, of Ag, Au, Cu, Al, Ni, Sn, Mg, Cr, Mo, Ti, Zr, Pt, Va, Rb, W, Zn, Ge, Te and Se, and mixtures or alloys thereof. Ag, Au, Cu, Al, Zn, Ni, Mo and Cr and mixtures or alloys thereof (for example bronzes and brasses) are preferred metals.

The term "metal derivatives" is intended to denote compounds derived from metals, especially oxides, fluorides, chlorides and sulfides.

As illustrations of these particles, mention may be made of aluminum particles, such as those sold under the names Starbrite 1200 EAC® by the company Siberline, and Metalure® by the company Eckart.

Mention may also be made of copper metal powders or alloy mixtures such as the reference 2844 sold by the company Radium Bronze, metallic pigments such as aluminum or bronze, such as those sold under the name Rotosafe 700 from the company Eckart, the silica-coated aluminum particles sold under the name Visionaire Bright Silver from the company Eckart and metal alloy particles, for instance the silica-coated bronze (alloy of copper and zinc) powders sold under the name Visionaire Bright Natural Gold from the company Eckart.

They may also be particles comprising a glass substrate, such as those sold by the company Nippon Sheet Glass under the name Microglass Metashine.

The goniochromatic coloring agent may be chosen, for example, from multilayer interference structures and liquid-crystal coloring agents.

Examples of symmetrical multilayer interference structures that may be used in the compositions prepared in accordance with the invention are, for example, the following structures: $Al/SiO_2/Al/SiO_2/Al$, pigments having this structure being sold by the company Dupont de Nemours; $Cr/MgF_2/Al/MgF_2/Cr$, pigments having this structure being sold under the name Chromaflair by the company Flex; $MoS_2/SiO_2/Al/SiO_2/MoS_2$; $Fe_2O_3/SiO_2/Al/SiO_2/Fe_2O_3$, and $Fe_2O_3/SiO_2/Fe_2O_3/SiO_2/Fe_2O_3$, pigments having these structures being sold under the name Sicopearl by the company BASF; $MOS_2/SiO_2/mica-Oxide/SiO_2/MoS_2$; $Fe_2O_3/SiO_2/mica-oxide/SiO_2/Fe_2O_3$; $TiO_2/SiO_2/TiO_2$ and $TiO_2/Al_2O_3/TiO_2$; $SnO/TiO_2/SiO_2/TiO_2/SnO$; $Fe_2O_3/SiO_2/Fe_2O_3$; $SnO/mica/TiO_2/SiO_2/TiO_2/mica/SnO$, pigments having these structures being sold under the name Xirona by the company Merck (Darmstadt). By way of example, these pigments may be the pigments of silica/titanium oxide/tin oxide structure sold under the name Xirona Magic by the company Merck, the pigments of silica/brown iron oxide structure sold under the name Xirona Indian Summer by the company Merck and the pigments of silica/titanium oxide/mica/tin oxide structure sold under the name Xirona Caribbean Blue by the company Merck. Mention may also be made of the Infinite Colors pigments from the company Shiseido. Depending on the thickness and the nature of the various layers, different effects are obtained. Thus, with the $Fe_2O_3/SiO_2/Al/SiO_2/Fe_2O_3$ structure, the color changes from green-golden to red-gray for $SiO_2$ layers of 320 to 350 nm; from red to golden for $SiO_2$ layers of 380 to 400 nm; from violet to green for $SiO_2$ layers of 410 to 420 nm; from copper to red for $SiO_2$ layers of 430 to 440 nm.

Examples of pigments with a polymeric multilayer structure that may be mentioned include those sold by the company 3M under the name Color Glitter.

Examples of liquid-crystal goniochromatic particles that may be used include those sold by the company Chemx and also the products sold under the name Helicone® HC by the company Wacker.

Filler

A composition according to the invention may comprise a filler, especially in a total content ranging from 0.01% to 30%, in particular from 0.01% to 20% by weight, for example ranging from 0.1% to 15% or from 0.5% to 10% by weight relative to the total weight of the composition.

For the purposes of the present invention, the term "fillers" should be understood as meaning colorless or white, mineral or synthetic particles of any form, which are insoluble in the medium of the composition irrespective of the temperature at which the composition is manufactured. These fillers serve especially to modify the rheology or texture of the composition.

The fillers may be mineral or organic and of any shape, platelet-shaped, spherical or oblong, irrespective of the crystallographic form (for example lamellar, cubic, hexagonal, orthorhombic, etc.). Mention may be made of talc, mica, silica, kaolin, polyimide (Nylon®) powder (Orgasol® from Atochem), poly-β-alanine powder and polyethylene powder, powders of tetrafluoroethylene polymers (Teflon®), lauroyllysine, starch, boron nitride, hollow polymer microspheres such as those of polyvinylidene chloride/acrylonitrile, for instance Expancel® (Nobel Industrie) or of acrylic acid copolymers (Polytrap® from the company Dow Corning) and silicone resin microbeads (Tospearls® from Toshiba, for example), elastomeric polyorganosiloxane particles, precipitated calcium carbonate, magnesium carbonate, magnesium hydrogen carbonate, hydroxyapatite, hollow silica microspheres (Silica Beads® from Maprecos), glass or ceramic microcapsules, and metal soaps derived from organic carboxylic acids containing from 8 to 22 carbon atoms and preferably from 12 to 18 carbon atoms, for example zinc stearate, magnesium stearate or lithium stearate, zinc laurate or magnesium myristate.

They may also be particles comprising a copolymer, said copolymer comprising trimethylol hexyllactone. In particular, it may be a copolymer of hexamethylene diisocyanate/trimethylol hexyllactone. Such particles are especially commercially available, for example, under the name Plastic Powder D-400® or Plastic Powder D-800® from the company Toshiki.

Additional Usual Cosmetic Ingredients

The composition according to the invention may also comprise any usual cosmetic ingredient, which may be chosen especially from antioxidants, fragrances, preserving agents, neutralizers, surfactants, sunscreens, sweeteners, vitamins, moisturizers, emollients, hydrophilic or lipophilic active agents, free-radical scavengers and sequestrants, and mixtures thereof.

Needless to say, a person skilled in the art will take care to select the optional additional ingredients and/or the amount thereof such that the advantageous properties of the composition according to the invention are not, or are not substantially, adversely affected by the envisioned addition.

Application Devices

Examples will now be given of devices for, inter alfa, implementing a cosmetic treatment process comprising the steps consisting in:

a) heating an application surface of a mass of solid product, using an artificial source of heat located to the exterior of the mass of product, especially an application surface of a wand of product, to bring it to a temperature above that of a portion of the mass of product remote from the application surface and which remains solid during the application, and b) applying the application surface thus heated to an area to be treated, especially the skin or the lips.

BRIEF DESCRIPTION OF DRAWINGS

The description of these devices is made with reference to the attached drawing, in which:

FIG. 1 shows schematically, in elevation, an example of a conditioning and application device made in accordance with the invention, FIG. 2 shows in isolation, with partial and schematic longitudinal cutaway, the cap of the device of FIG. 1, FIG. 3 illustrates, schematically and partially, the heating of the wand by contact with a hot surface, FIG. 4 represents, schematically and partially, one embodiment example of the heating member, FIGS. 5 to 7 illustrate production details of variants of heating members, FIG. 8 represents, schematically, an embodiment variant of the conditioning and application device, FIG. 9 is a schematic and partial cutaway of the device of FIG. 8, after insertion in the corresponding housing of the case, FIG. 10 shows a wand and associated support means, FIG. 11 shows in elevation an embodiment variant of the conditioning and application device, FIG. 12 is a partial and schematic longitudinal cutaway of the device of FIG. 11, FIG. 13 is a partial and schematic longitudinal cutaway of an embodiment variant of the device, FIG. 14 is a product conditioning variant, and FIG. 15 described previously illustrates the measurement of the coefficient of dynamic fraction.

Figure 15:
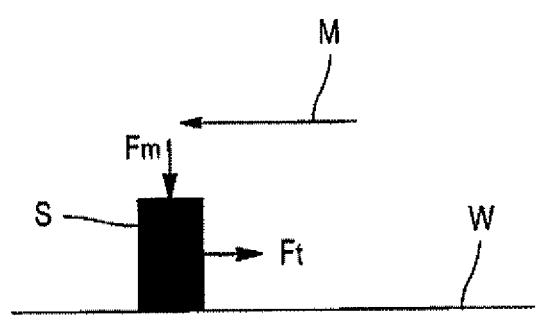

The conditioning and application device 1 shown in FIG. 1 comprises a base part 2 that supports a mass of product according to the invention in the form of a wand S of product, and a cap 3 and that can be attached to the base part 2 to close the device 1 when not in use.

The base part 2 may be of any known type for removing the wand S gradually as it is consumed.

The base part 2 comprises, for example, two parts 5 and that can rotate relative to each other, and a mechanism for transforming the relative rotation of the two parts 5 and 6 into an axial movement along the longitudinal axis X of the wand S.

The wand S is borne, for example, in this mechanism, by a cup 58 as shown in FIG. 10, comprising spurs 59 engaged in two pieces belonging, respectively, to parts 5 and 6, one of which comprises longitudinal rectilinear slits and the other spiral slits, such that a rotation of these two pieces is accompanied by an axial movement of the cup and of the wand S.

Examples of mechanisms that may be suitable for use are described in the publications U.S. Pat. No. 6,340,258, U.S. Pat. No. 6,086,276, U.S. Pat. No. 6,371,673, U.S. Pat. No. 5,171,096 and U.S. Pat. No. 7,293,926, the content of which is incorporated herein by reference.

The cap 3 comprises a heating device 10 for heating the end 11 of the wand S prior to its application to the keratin materials, for example the skin or the lips.

The heating device 10 may house a power source, not shown, for example containing one or more batteries or accumulators, and a heating member comprising, for example, an electrical resistance powered by the power source.

Examples of heating members that may be suitable for use are disclosed in US 2007/0 286 665 A1, for example. The heating member is arranged so as to raise the temperature of a heating surface 13 which, in the example of FIGS. 1 and 2, may come into contact with the wand S, as shown in FIG. 3, so as to raise the temperature of the distal end 11 thereof.

The heating device 10 may comprise a switch 14 that allows the user to switch the heating device 10 on or off, and also an operating indicator 15, for example an indicator light that lights up when the heating surface 13 is undergoing heating.

The heating device 10 may optionally comprise any means for regulating the temperature of the heating surface 13, so that it does not exceed a predefined value.

When the heating surface is inaccessible to the user, a heating temperature that is higher but compatible with the product may be accepted. On the other hand, when the heating surface 13 may come into contact with the user, a temperature not exceeding 65° C. is preferred.

The heating device 10 may also, where appropriate, comprise a timer for heating the end 11 of the wand S only for a predefined time, so as to avoid premature wear of the electrical power source and/or to avoid bringing the wand assembly to an excessive temperature.

The heating device 10 may advantageously comprise any suitable sensor for preventing the start of functioning of the heating except in the case of effective contact of the heating surface with the end 11 of the wand S.

For example, the heating device 10 may comprise a contact pressure sensor between the heating surface 13 and the wand S, and permit heating of the heating surface 13 only in the case of veritable contact with the wand S.

The heating surface 13 may be defined, for example, by a contact piece 20, which is, for example, axially mobile along the axis X relative to the body 22 of the heating device 10 against the return action of an elastic return member 23, for instance a spring housed inside the contact piece 20, as illustrated in FIG. 4.

This FIG. 4 shows a heating device comprising an electrical resistance 25 placed in the bottom of the contact piece 20, so as to be as close as possible to the heating surface 13.

The contact piece 20 may comprise, for example, a metal that is a good heat conductor, with a low wall thickness, so as to have low thermal inertia. In certain embodiments, the contact piece 20 may, for example, comprise aluminum.

The heating surface 13 may be given any shape adapted to the geometry of the end 11 of the wand, for example a beveled shape substantially complementary to the shape of the end 11 of the wand S, as illustrated in FIGS. 1 and 2, or another shape, for example a concave shape toward the wand S, especially a spherical crown shape as illustrated in FIG. 5, a conical or frustoconical shape as illustrated in FIG. 6, or a substantially flat shape perpendicular to the axis X, as illustrated in FIG. 7.

When the shape of the heating surface 13 is not rotationally symmetric about the axis X, the device 1 may comprise rotational indexing means for the base part 2 and the cap 3 so as to enable attachment of the cap 3 to the base part 2 only in one predefined angular orientation between the two, in which the heating surface can come to rest in a predefined manner, which is compatible with its geometry, against the wand S.

The wand S, which is, for example, a lipstick wand, may have a cross section of between 0.1 and 5 cm$^2$, or even between 0.15 and 1 cm$^2$, and the device 1 may be used by first switching on the heating device 10 and then waiting for the time necessary for the end 11 of the wand that defines the application surface to be brought to the desired temperature.

Arrival at the operating temperature may be indicated, for example, by the indicator light 15, which may pass, for example, from being a continuous light indicating the startup of the device, to a flashing light or a color change when the temperature is reached. Other methods for indicating the operating state may be used without, however, departing from the scope of the invention.

Once the end of the wand has been heated, the base part 2 may be separated from the cap 3 and the user can apply the product of the wand onto the lips or other keratin materials. Softening of the product at the end 11 of the wand ensures comfortable application and good transfer onto the lips, with a thick and optionally glossy deposit on application.

For example, the application is performed without using an applicator. In other words, only the composition, and more precisely the softened surface, comes into direct contact with the area to be treated.

The body of the wand S is at room temperature or at a slightly higher temperature, but insufficient to compromise the mechanical strength necessary to withstand the mechanical efforts generated by the application. The temperature difference between the application surface and the body of the wand, especially at the end opposite the application surface, is, for example, at least 20° C., or even at least 30° C. when the wand has its initial length, on the first use.

The device 1 may be used in a similar manner for making up the skin, and the wand may then be of greater cross section, where appropriate.

It may be that the heating device is not incorporated into a cap 3 of the conditioning device, but is present in a case 40 separate from the conditioning device of the wand S, as illustrated in FIGS. 8 and 9.

The case 40 may house a power source and/or may comprise a means for connecting to a power source, for example the mains supply, via a low-voltage transformer.

The case 40 may also comprise startup means 41, for instance an on/off switch, and also one or more indicator lights 42 and 55 to indicate the live power connection and/or the end of arrival at the operating temperature.

In the example of FIGS. 8 and 9, the case 40 comprises an aperture 46 into which the base part 2 may be at least partially introduced, as illustrated in FIG. 9, so as to bring the end 11 of the wand in the vicinity of a heating means 50 present in the case 40.

The aperture 46 has, for example, a cross section adapted to one of the pieces of the base part, so that the engagement of the base part in the case brings the end 11 of the wand into a predefined position, according to at least two spatial directions, relative to the heating means.

The case 40 may comprise any suitable sensor 51 for detecting the insertion of the base part 2 into the case 40 and optionally the positioning of the wand relative to the heating means.

Heating of the end of the wand S may take place by conduction, on contact with a hot surface, in the manner described above. In this case, the heating means comprises a heating surface that may be brought to the appropriate temperature by any heating means, for example an electrical resistance.

Heating of the end of the wand may also be performed without contact, for example by infrared radiation and/or convection, and/or by vibrations and/or wireless radiation, or any other source that produces heat.

As mentioned above, the case 40 may comprise any suitable sensor, especially an optical sensor, that is capable of evaluating the distance between the end 11 of the wand and the heating means 50, so as to switch on the heating means only when a predefined distance is respected and/or so as to control the heating power as a function of the remoteness between the heating means and the end of the wand S.

In certain variants, the heating means 50 may be a system of heating by emission of infrared radiation toward the end 11 of the wand, for example using a halogen or incandescent lamp, or by blowing hot air toward the end 11.

In certain variants, the end 11 of the wand S may also be heated by exposure to wireless radiation, for example microwaves, focused at the end 11 of the wand S.

In yet other variants, the end 11 of the wand S may be heated by ultrasonic vibrations.

In the embodiment variant of FIGS. 11 and 12, the heating device 60 comprises a heating means 62 that is an integral part of the base part 2 and that may comprise, as illustrated, a circular-shaped heating member 62, through which the wand S may pass. The heating member 62 has, for example, a cross section greater than or equal to that of the wand S.

The heating device 60 may comprise, for example, a control member 64 which the user may press to start the functioning of the heating member 62. The heating member 62 may comprise, for example, a heating resistance for heating the end 11 of the wand S by conduction, convection and/or radiation (for example infrared, microwave, etc. radiation).

Where appropriate, the heating member 62 may also participate in the application of the product associated with the wand S, and, to this end, may have a top face 70 of suitable shape, for example beveled.

To use the device in the example under consideration, the user can bring the end 11 of the wand to the heating member 62 and start the heating by pressing on the control member 64.

The heating device may comprise an indicator light 72 that indicates to the user that the heating member 62 is functioning.

The user can then stop the heating when he visually observes that the end 11 of the wand has become changed in appearance following the raising of the temperature, for example when it has become glossy.

The user can then optionally, at this moment, move the end 11 slightly higher upward so as to facilitate the application of the product, without contact with the heating member 62. As a variant, the user can apply the product via contact not only of the wand 8, but also of the heating member 62, on the lips or the skin.

Where appropriate, the surface of the heating member 62 liable to come into contact with the skin may be flocked or may have a textured surface aspect that facilitates application.

In the variant shown in FIG. 13, the wand S passes through a heating member 62 defining an aperture 76 whose cross section is narrower than the cross section of the body of the wand.

Softening of the wand S on contact with the heating member 62 may thus be accompanied, in this example, by a deformation of the wand through the heating member 62. This may increase the precision of application of the product and prevent the wand S from being advanced relative to the heating member 62 before sufficient softening has been reached.

The outer surface of the heating member 62 may be tapered, as shown in FIG. 13, so as to reduce the contact surface between the treated area and the heating member 62.

FIG. 14 shows an embodiment variant in which the mass of product S associated with the wand S is supported by a stem 200, and is suitable, for example, for single use.

The application surface 202 is heated by being brought, for example, into contact with or in the vicinity of a hot surface, for example by introducing it into a case equipped with a heating means such as the case described previously with reference to FIGS. 8 and 9.

In the present text, the contents, unless otherwise mentioned, are expressed on a weight basis relative to the total weight of the composition.

The invention is illustrated in greater detail in the examples described below, which are given as nonlimiting illustrations. The percentages are weight percentages. In the examples that follow, the weight percentages are indicated relative to the total weight of the composition.

EXAMPLE

Lipstick Composition

Protocol:

The pigments of phase D are ground in phase A.

The ground material and the ingredients of phase B are introduced into a jacketed heating pan. The whole is heated at 98-100° C. with Rayneri stirring until all of the ingredients have melted.

Phase C is added with Rayneri stirring until a uniform mixture is obtained.

Finally, the nacre and the fragrance (phase B) are added to the mixture, which is poured into a lipstick mold 11.06 mm in diameter. The mold is then placed at −20° C. for 30 minutes, and the sticks are then removed from the mold.

| Phase | Ingredients | Weight % |
|---|---|---|
| A | Octyldodecanol [1] | 6.59 |
| A | Bis(diglyceryl) poly(2-acyladipate) [2] | 55.19 |
|   | Bis-behenyl/isostearyl/phytosteryl dimer dilinoleyl dimer dilinoleate [3] | 22.68 |
|   | Polyethylene [4] | 4.79 |
|   | Poly(C10-30)alkyl acrylate [5] | 5.00 |
| C | Silica dimethyl silylate [6] | 1.5 |
| D | Yellow 6 Lake | 2.06 |
|   | Blue 1 Lake | 0.13 |
|   | Red 7 | 0.47 |
|   | Titanium dioxide [7] | 2.19 |
|   | Iron oxides | 0.26 |
| E | Mica (and) titanium dioxide (and) iron oxides [8] | 1.60 |
|   | Fragrance | 0.05 |
|   | TOTAL | 100 |

[1] Eutanol G sold by the company Cognis
[2] Softisan 649 sold by the company Sasol
[3] Plandool-G sold by the company Nippon Fine Chemical
[4] Performalene 500-L from New Phase Technologies
[5] Intelimer IPA 13-1 sold by the company Air Products and Chemicals
[6] Aerosil R 972 sold by the company Evonik-Degussa
[7] Tipaque PF-671 sold by the company Ishihara Sangyo
[8] Cloisonne Sparkle Gold 222 J sold by the company BASF The hardness at 20° C. of the stick is 187 $Nm^{-1}$.

At room temperature, the composition thus obtained deposits very sparingly and is very dragging.

In order to illustrate the invention, the bevel of the composition is placed in contact with a hot source at 60° C. for 10 seconds and then applied to the lips: the application is more pleasant compared with the application performed at room temperature as outlined above. Furthermore, the deposit is thicker, very glossy and has good gloss remanence.

What is claimed is:

1. A nontherapeutic method for applying lipstick, comprising:
bringing an outer surface of a piece of lipstick composition into contact with or in the vicinity of a heating device so as to heat said piece of lipstick composition locally-to soften essentially only said outer surface and to lower its coefficient of dynamic friction, and
then applying the outer surface of the lipstick composition thus heated,
said lipstick composition comprising, in a physiologically acceptable medium:
at least 4% by weight, relative to the total weight of the lipstick composition, of at least one structuring agent, said structuring agent selected from the group consisting of waxes, organophilic clays, hydrophobic fumed silicas, block copolymers resulting from the polymerization or copolymerization of at least one monomer containing an ethylenic group, and mixtures thereof, less than 10% by weight of glossy oil(s), relative to the total weight of the lipstick composition, said oil(s) being hydrocarbon-based oil(s) and/or silicone oil(s) with a molecular mass of greater than 400 g/mol; and less than 20% by weight of fluid oil relative to the total weight of the lipstick composition, wherein the heating device comprises batteries or accumulators as a source of electrical power.

2. The method as claimed in claim 1, in which the lipstick composition comprises said structuring agent in a content ranging from 4% to 40% by weight, relative to the total weight of the solid cosmetic composition.

3. The method as claimed in claim 1, in which the lipstick composition comprises said structuring agent(s) in a content ranging from 4% to 25% by weight, relative to the total weight of the solid cosmetic composition.

4. The method as claimed in claim 1, in which the structuring agent is a mixture of (1) waxes and (2) hydrophobic fumed silicas and/or organophilic clays.

5. The method as claimed in claim 1, in which the lipstick composition has a temperature-sensitive coefficient of dynamic friction of greater than or equal to 0.5 at 25° C.

6. The method as claimed in claim 1, in which the lipstick composition has a hardness of greater than or equal to 80 $Nm^{-1}$ at 20° C.

7. The method as claimed in claim 1, in which the lipstick composition has a hardness of greater than or equal to 120 $Nm^{-1}$.

8. The method as claimed in claim 1, in which said coefficient of dynamic friction is, at the temperature to which the lipstick composition is heated, less than or equal to 0.45.

9. The method as claimed in claim 1, in which the lipstick composition comprises at least one hydrocarbon-based glossy oil with a molar mass of greater than or equal to 400 g/mol.

10. The method as claimed in claim 1, in which the lipstick composition comprises at least one hydrocarbon-based glossy oil with a molar mass of greater than or equal to 650 g/mol.

11. The method as claimed in claim 1, in which the lipstick composition comprises at least one hydrocarbon-based glossy oil with a molar mass ranging from 1,000 to 5,000 g/mol.

12. The method as claimed in claim 1, in which the lipstick composition is in the form of a wand with a diameter of greater than or equal to 8 mm.

13. The method as claimed in claim 1, in which the lipstick composition comprises at least one semi-crystalline polymer of organic structure whose melting point is greater than or equal to 30° C.

* * * * *